United States Patent [19]
de Sauvage et al.

[11] Patent Number: 6,136,958
[45] Date of Patent: Oct. 24, 2000

[54] ANTIBODIES TO VERTEBRATE SMOOTHENED PROTEINS

[75] Inventors: Frederic J. de Sauvage, Foster City; Arnon Rosenthal, Burlingame; Donna M. Stone, Brisbane, all of Calif.

[73] Assignee: Genentech, Inc., South San Francisco, Calif.

[21] Appl. No.: 08/953,823

[22] Filed: Sep. 30, 1997

Related U.S. Application Data
[60] Provisional application No. 60/027,070, Sep. 30, 1996.

[51] Int. Cl.$^7$ .................................................. C07K 16/28
[52] U.S. Cl. ................................ 530/388.22; 530/387.1; 530/387.9; 530/388.1; 530/530; 536/23.5
[58] Field of Search ............................. 530/387.1, 387.9, 530/388.1, 388.22, 389.1, 350; 536/23.5; 424/130.1, 139.1, 141.1, 143.1

[56] References Cited

U.S. PATENT DOCUMENTS

| | | |
|---|---|---|
| 4,676,980 | 6/1987 | Segal et al. . |
| 4,816,567 | 3/1989 | Cabilly et al. . |
| 5,364,934 | 11/1994 | Drayna et al. . |

FOREIGN PATENT DOCUMENTS

| | | |
|---|---|---|
| 003089 | 7/1979 | European Pat. Off. . |
| WO 87/05330 | 9/1987 | WIPO . |
| WO 91/00360 | 1/1991 | WIPO . |
| WO 92/20373 | 11/1992 | WIPO . |
| WO 93/08829 | 5/1993 | WIPO . |
| WO 94/04679 | 3/1994 | WIPO . |
| WO 94/04690 | 3/1994 | WIPO . |
| WO 94/29348 | 12/1994 | WIPO . |

OTHER PUBLICATIONS

Alcedo et al., The drosophila smoothened gene encodes a seven–pass membrane protein, a putative receptor for the hedgehog signal, Cell, 86(2): 221–232 (Jul. 1996).

Perrimon, N., Serpentine proteins slither into the wingless and hedgehog fields, Cell, 86(4): 513–516 (Aug. 1996).

Hooper, J.E., Distinct pathways for autocrine and paracrine Wingless signalling in drosophila embryos, Nature, 372(6505): 461–464 (Dec. 1994).

Stone et al., "The tumour–suppressor gene patched encodes a candidate receptor for Sonic hedgehog" *Nature* 384(14):129–134 (Nov. 1996).

Handbook of Monoclonal Antibodies, Ferrone et al. ed., Park Ridge, NJ:Noyes Publications, pp. 302–359 and Chapter 22 (1985).

Tissue Culture, Kruse and Patterson, eds., Academic Press (1973).

Remington's Pharmaceutical Sciences, Oslo et al., eds., 16th edition, Mack Publishing Co. (1980).

Bejsovec and Wieschaus, "Segment polarity gene interactions modulate epidermal patterning in Drosophila embryos" *Development* 119:501–517 (1993).

Bhanot et al., "A New Member of the Frizzled Family From Drosophila Functions As A Wingless Receptor" *Nature* 382:225–230 (1996).

Bitgood et al., "Sertoli Cell Signaling by Desert Hedgehog Regulates the Male Germline" *Current Biology* 6(3):298–304 (1996).

Brodeur et al., "Mouse–Human Myeloma Partners for the Production of Heterohybridomas" *Monoclonal Antibody Production Techniques and Applications*, New York: Marcel Dekker, Inc. pp. 51–63 (1987).

(List continued on next page.)

*Primary Examiner*—Lorraine Spector
*Assistant Examiner*—Claire M. Kaufman
*Attorney, Agent, or Firm*—Craig G. Svoboda

[57] ABSTRACT

Novel vertebrate homologues of Smoothened, including human and rat Smoothened, are provided. Compositions including vertebrate Smoothened chimeras, nucleic acid encoding vertebrate Smoothened, and antibodies to vertebrate Smoothened, are also provided.

13 Claims, 24 Drawing Sheets

(3 of 24 Drawing Sheet(s) Filed in Color)

OTHER PUBLICATIONS

Chan et al., "Two Homologs of the Drosophila Polarity Gene Frizzled (fz) Are Widely Expressed in Mammalian Tissues" *Journal Biological Chemistry* 267(35):25202–25207 (1992).

Cole et al., "The EBV–Hybridoma Technique and Its Application to Human Lung Cancer" *Monoclonal Antibodies and Cancer Therapy*, Reisfeld et al., New York:Alan R. Liss, Inc. pp. 77–96 (1985).

Currie and Ingham, "Induction of a specific muscle cell type by a hedgehog–like protein in zebrafish" *Nature* 382:452–455 (1996).

David et al., "Protein Iodination with Solid State Lactoperoxidase" *Biochemistry* 13(5):1014–1021 (1974).

Davis et al., "Released form of CNTF receptor alpha component as a soluble mediator of CNTF responses" *Science* 259:1736–1739 (1993).

Dieffenbach et al., *PCR Primer: A Laboratory Manual*, Cold Spring Harbor Laboratory Press pp. 1–16;133–142 (1995).

DiNardo et al., "Two–tiered regulation of spatially patterned engrailed gene expression during Drosophila embrogenesis" *Nature* 332:604–609 (1988).

Echelard et al., "Sonic hedgehog, a member of a family of putative signaling molecules, is implicated in the regulation of CNS polarity" *Cell* 75:1417–1430 (1993).

Fan et al., "Long–range sclerotome induction by sonic hedgehog: direct role of the amino–termial cleavage product and modulation by the cyclic AMP signaling pathway" 81:457–465 (1995).

Fiers et al., "Complete Nucleotide Sequence of SV40 DNA" *Nature* 273:113–120 (May 11, 1978).

Gailani et al., "The role of the Human Homologue of Drosophila Patched in Sporadic Basal Carcinomas"*Nature Genetics* 13(5) (1996).

Goodrich et al., "Conservation of the hedgehog/patched signaling from flies to mice: induction of a mouse patched gene by Hedgehog" *Genes Dev.* 10(3):301–312 (1996).

Hahn et al., "Mutations of the Human Homolog of Drosophila Patched in the Nevoid Basal Cell Carcinoma Syndrome" *Cell* 85:841–851 (1996).

Hidalgo and Ingham, "Cell patterning in the Drosophila segment: spatial regulation of the segment polarity gene patched" *Development* 110:291–301 (1990).

Hooper and Scott, "The Drosophila patched gene encodes a putative membrane protein required for segmental patterning" *Cell* 59:751–765 (1989).

Hunter et al., "Preparation of Iodine 131 Labelled Human Growth Hormone of High Specific Activity" *Nature* 194:495–496 (1962).

Hynes et al., "Control of neuronal diversity by the floor plate:contact–mediated induction of midbrain dopaminergic neurons", *Cell* 80:95–101 (1995).

Ingham and Hidalgo, "Regulation of wingless transcription in the Drosophila embryo" *Development* 117:283–291 (1993).

Ingham et al., "Role of the Drosophila patched gene in positional signalling" *Nature* 353:184–187 (1991).

Ingham et al., "Signalling by hedgehog family proteins in Drosophila and vertebrate devlopment" *Curr. Optin. Genet. Dev.* 5:492–498 (1995).

Johnson et al., "Ectopic expression of Sonic hedgehog alters dorsal–ventral patterning of somites" *Cell* 79:1165–1173 (1994).

Johnson et al., "Human Homolog of Patched, a Candidate Gene for the Basal Cell Nevus Syndrome" *Science* 272:1668–1671 (1996).

Jurgens et al., "Mutations Affecting the Pattern of the Larval Cuticle in Drosophila–Melanogaster.II. Zygotic Loci on the Third Chromsome" *Wilhelm Roux's Archives of Developmental Biology* 193(5):283–295 (1984).

Kinzler et al., "Identification of an amplified, highly expressed gene in a human glioma" *Science* 236:70–73 (1987).

Klein et al., "Selection for Genes Encoding Secreted Proteins and Receptors" *Pro. Natl. Acad. Sci. USA* 93:7108–7113 (Jul. 1996).

Krauss et al., "A functionally coserved homolog of the Drosophila segment polarity gene hh is expressed in tissues with polarizing activity in zebrafish embryos" *Cell* 75:1431–1444 (1993).

Lee et al., "Autoproteolysis in hedgehog protein biogenesis" *Science* 266:1528–1537 (1994).

Lindsley and Zimm *The Genome of Drosophila Melanogaster*, San Diego, CA:Academic Press (1992).

Lumsden and Graham, "A Forward Role for Hedgehog" *Current Biology* 5(12):1347–1350 (1995).

Marigo et al., "Conservation in hedgehog signaling: induction of a chicken patched homolog by Sonic hedgehog in the developing limb" *Development* 122:1225–1233 (1996).

Milstein et al., "Hybrid Hybridomas and Their Use in Immunohistochemistry" *Nature* 305:537–540 (1983).

Nakano et al., "A protein with several possible membrane–spanning domains encoded by the Drosophila segment polarity gene patched" *Nature* 341:508–513 (1989).

Nusslein–Volhard et al., "Mutations Affecting the Pattern of the Larval Cuticle in Drosophila–Melanogaster" *Wilhelm Roux's Archives of Developmental Bipology* 193(5):267–282 (1984).

Nygren, H., "Conjugation of Horseradish Peroxidase to Fab Fragments with Diffrent Homobifunctional and Heterobifunctional Cross–Linking Reagents" *The Journal of Histochemistry and Cytochemistry* 30(5):407–412.

Pain et al., "Preparation of Protein A–Peroxidase Monoconjugate Using a Heterobifunctional Reagent, and its Use in Enzyme Immunoassays" *Journal of Immunological Methods* 40:219–230 (1981).

Pennisi, E., "Gene Linked to Commonest Cancer" *Science* 272:1583–1584 (1996).

Perrimon, N., "The genetic basis of patterned baldness in Drosophila" *Cell* 76:781–784 (1994).

Perrimon, N., "Hedgehog and Beyond" *Cell* 80:517–520 (1995).

Riddle et al., "Sonic hedgehog mediates the polarizing activity of the ZPA" *Cell* 75:1401–1416 (1993).

Rijsewijk et al., "The Drosophila homolog of the mouse mammary oncogene int–1 is identical to the segment polarity gene wingless" *Cell* 50:649–657 (1987).

Roberts et al., "Sonic hedgehog is an endodermal signal inducing Bmp–4 and Hox genes during induction and regionalization of the chick hindgut" *Development* 121:3163–3174 (1995).

Roelink et al., "Floor plate and motor neuron induction by vhh–1, a vertebrate homolog of hedgehog expressed by the notochord" *Cell* 76:761–775 (1994).

Sambrook et al. Molecular Cloning: A Laboratory Manual, Second Edition edition, New York:Cold Spring Harbor Laboratory Press (1989).

Smith et al., "Cardiac Glycoside–Specific Antibodies in the Treatment of Digitalis Intoxication" *Antibodies in Human Diagnosis and Therapy* pp. 365–389 (1977).

Tabata and Kornberg, "Hedgehog is a signaling protein with a key role in patterining Drosophila imaginal discs" *Cell* 76:89–102 (1994).

Treanor et al., "Characterization of a multicomponent receptor for GDNF" *Nature* 382:80–83 (1996).

Van den Heuvel and Ingham, "Smoothened Encodes a Receptor–Like Serpentine Protein Required for Hedgehog Signalling" *Nature* 382:547–551 (1996).

Vortkamp et al., "Regulation of rate of cartilage differentiation by Indian hedgehog and PTH–related protein" *Science* 273:613–622 (1996).

Zola, "Using Monoclonal Antibodies: Soluble Antigens" *Monoclonal Antibodies: A Manual of Techniques*, CRC Press, Chapter 6, pp. 147–158 (1987).

```
GCGGCGCGCT CGCGCGGAGG TGGCTGCTGG GCCGCGGGCT GGCGTGGGGG 50

CGGAGCCGGG GAGCGACTCC CGCACCCCAC GGCCGGTGCC TGCCCTCCAT 100

CGAGGGGCTG GGAGTTAGTT TTAATGGTGG GAGAGGGAAT GGGGCTGAAG 150

ATCGGGGCCC CAGAGGGTTC CCAGGGTTGA AGACAATTCC AATCGAGGCG 200

AGGGAGTCCG GGGTCCGTGC ATCCTGGCCC GGGCCTGCGC AGCTCAACAT 250

GGGGCCCGGG TTCCAAAGTT TGCAAAGTTG GGAGCCGAGG GGCCCGGACG 300

CGCGCGGCGC CTGGCGAAAG CTGGCCCCAG ACTTTCGGGG CGCACCGGTC 350

GCCTAAGTAG CCTCCGCGGC CCCCGGGGTC GTGTGTGTGG CCAGGGGACT 400

CCGGGGAGCT CGGGGGCGCC TCAGCTTCTG CTGAGTTGGC GGTTTGGCC  449
```

```
ATG GCT GCT GGC CGC CCC GTG CGT GGG CCC GAG CTG GCG  488
Met Ala Ala Gly Arg Pro Val Arg Gly Pro Glu Leu Ala
 1           5                   10

CCC CGG AGG CTG CTG CAG TTG CTG CTG CTG GTA CTG CTT  527
Pro Arg Arg Leu Leu Gln Leu Leu Leu Leu Val Leu Leu
     15                  20                  25

GGG GGC CGG GGC CGG GGG GCG GCC TTG AGC GGG AAC GTG  566
Gly Gly Arg Gly Arg Gly Ala Ala Leu Ser Gly Asn Val
             30                  35

ACC GGG CCT GGG CCT CGC AGT GCC GGC GGG AGC GCG AGG  605
Thr Gly Pro Gly Pro Arg Ser Ala Gly Gly Ser Ala Arg
 40                  45                  50

AGG AAC GCG CCG GTG ACC AGC CCT CCG CCG CTG CTG       644
Arg Asn Ala Pro Val Thr Ser Pro Pro Pro Leu Leu
         55                  60                  65

AGC CAC TGC GGC CGG GCC GCC CAC TGC GAG CCT TTG CGC  683
Ser His Cys Gly Arg Ala Ala His Cys Glu Pro Leu Arg
                 70                  75

TAC AAC GTG TGC CTG GGC TCC GCG CTG CCC TAC GGA GCC  722
Tyr Asn Val Cys Leu Gly Ser Ala Leu Pro Tyr Gly Ala
         80                  85                  90

ACC ACC ACG CTG CTG GCT GGG GAC TCG GAC TCG CAG GAG  761
Thr Thr Thr Leu Leu Ala Gly Asp Ser Asp Ser Gln Glu
                 95                  100

GAA GCG CAC AGC AAG CTC GTG CTC TGG TCC GGC CTC CGG  800
Glu Ala His Ser Lys Leu Val Leu Trp Ser Gly Leu Arg
105                  110                  115
```

FIG._1A

```
AAT GCT CCC CGA TGC TGG GCA GTG ATC CAG CCC CTG CTG  839
Asn Ala Pro Arg Cys Trp Ala Val Ile Gln Pro Leu Leu
        120             125             130

TGT GCT GTC TAC ATG CCC AAG TGT GAA AAT GAC CGA GTG  878
Cys Ala Val Tyr Met Pro Lys Cys Glu Asn Asp Arg Val
                135             140

GAG TTG CCC AGC CGT ACC CTC TGC CAG GCC ACC CGA GGC  917
Glu Leu Pro Ser Arg Thr Leu Cys Gln Ala Thr Arg Gly
        145             150             155

CCC TGT GCC ATT GTG GAG CGG GAA CGA GGG TGG CCT GAC  956
Pro Cys Ala Ile Val Glu Arg Glu Arg Gly Trp Pro Asp
                160             165

TTT CTG CGT TGC ACG CCG GAC CAC TTC CCT GAA GGC TGT  995
Phe Leu Arg Cys Thr Pro Asp His Phe Pro Glu Gly Cys
170             175             180

CCA AAC GAG GTA CAA AAC ATC AAG TTC AAC AGT TCA GGC  1034
Pro Asn Glu Val Gln Asn Ile Lys Phe Asn Ser Ser Gly
        185             190             195

CAA TGT GAA GCA CCC TTG GTG AGG ACA GAC AAC CCC AAG  1073
Gln Cys Glu Ala Pro Leu Val Arg Thr Asp Asn Pro Lys
                200             205

AGC TGG TAC GAG GAC GTG GAG GGC TGT GGG ATC CAG TGC  1112
Ser Trp Tyr Glu Asp Val Glu Gly Cys Gly Ile Gln Cys
        210             215             220

CAG AAC CCG CTG TTC ACC GAG GCT GAG CAC CAG GAC ATG  1151
Gln Asn Pro Leu Phe Thr Glu Ala Glu His Gln Asp Met
                225             230

CAC AGT TAC ATC GCA GCC TTC GGG GCG GTC ACC GGC CTC  1190
His Ser Tyr Ile Ala Ala Phe Gly Ala Val Thr Gly Leu
235             240             245

TGT ACA CTC TTC ACC CTG GCC ACC TTT GTG GCT GAC TGG  1229
Cys Thr Leu Phe Thr Leu Ala Thr Phe Val Ala Asp Trp
        250             255             260

CGG AAC TCC AAT CGC TAC CCT GCG GTT ATT CTC TTC TAT  1268
Arg Asn Ser Asn Arg Tyr Pro Ala Val Ile Leu Phe Tyr
                265             270

GTC AAT GCG TGT TTC TTT GTG GGC AGC ATT GGC TGG CTG  1307
Val Asn Ala Cys Phe Phe Val Gly Ser Ile Gly Trp Leu
        275             280             285
```

FIG._1B

```
TAC TAT GCC TTG ATG GCT GGA GTA GTG TGG TTC GTG GTC  1463
Tyr Tyr Ala Leu Met Ala Gly Val Val Trp Phe Val Val
            330                 335

CTC ACC TAT GCC TGG CAC ACC TCC TTC AAA GCC CTG GGC  1502
Leu Thr Tyr Ala Trp His Thr Ser Phe Lys Ala Leu Gly
    340                 345                 350

ACC ACT TAC CAG CCT CTC TCG GGC AAG ACA TCC TAT TTC  1541
Thr Thr Tyr Gln Pro Leu Ser Gly Lys Thr Ser Tyr Phe
            355                 360

CAC CTG CTC ACG TGG TCA CTC CCC TTC GTC CTC ACT GTG  1580
His Leu Leu Thr Trp Ser Leu Pro Phe Val Leu Thr Val
365                 370                 375

GCA ATC CTT GCT GTG GCT CAG GTA GAT GGG GAC TCC GTG  1619
Ala Ile Leu Ala Val Ala Gln Val Asp Gly Asp Ser Val
            380                 385                 390

AGT GGC ATC TGC TTT GTA GGC TAC AAG AAC TAT CGG TAC  1658
Ser Gly Ile Cys Phe Val Gly Tyr Lys Asn Tyr Arg Tyr
                395                 400

CGT GCT GGC TTT GTA CTT GCC CCA ATT GGC CTG GTG CTT  1697
Arg Ala Gly Phe Val Leu Ala Pro Ile Gly Leu Val Leu
    405                 410                 415

ATT GTG GGA GGC TAC TTC CTC ATC CGA GGG GTC ATG ACT  1736
Ile Val Gly Gly Tyr Phe Leu Ile Arg Gly Val Met Thr
            420                 425

CTG TTC TCC ATC AAG AGC AAC CAC CCT GGG CTT CTG AGT  1775
Leu Phe Ser Ile Lys Ser Asn His Pro Gly Leu Leu Ser
430                 435                 440

GAG AAG GCA GCC AGC AAG ATC AAT GAG ACC ATG CTG CGC  1814
Glu Lys Ala Ala Ser Lys Ile Asn Glu Thr Met Leu Arg
            445                 450                 455

CTG GGC ATT TTT GGC TTC CTC GCC TTT GGC TTC GTG CTC  1853
Leu Gly Ile Phe Gly Phe Leu Ala Phe Gly Phe Val Leu
                460                 465

ATC ACC TTC AGC TGC CAC TTC TAT GAC TTC TTC AAC CAG  1892
Ile Thr Phe Ser Cys His Phe Tyr Asp Phe Phe Asn Gln
    470                 475                 480

GCT GAG TGG GAG CGT AGC TTC CGG GAC TAT GTG CTA TGC  1931
Ala Glu Trp Glu Arg Ser Phe Arg Asp Tyr Val Leu Cys
            485                 490
```

FIG._1C

```
CAA GCC AAT GTG ACC ATT GGG CTG CCT ACC AAG AAG CCC  1970
Gln Ala Asn Val Thr Ile Gly Leu Pro Thr Lys Lys Pro
495              500                 505

ATT CCT GAT TGT GAG ATC AAG AAT CGG CCC AGC CTC CTG  2009
Ile Pro Asp Cys Glu Ile Lys Asn Arg Pro Ser Leu Leu
        510                 515                 520

GTG GAG AAG ATC AAT CTG TTT GCC ATG TTT GGC ACT GGC  2048
Val Glu Lys Ile Asn Leu Phe Ala Met Phe Gly Thr Gly
                525                 530

ATT GCC ATG AGC ACC TGG GTC TGG ACC AAG GCC ACC CTG  2087
Ile Ala Met Ser Thr Trp Val Trp Thr Lys Ala Thr Leu
535              540                 545

CTC ATC TGG AGG CGC ACC TGG TGC AGG TTG ACT GGG CAC  2126
Leu Ile Trp Arg Arg Thr Trp Cys Arg Leu Thr Gly His
        550                 555

AGT GAT GAT GAA CCC AAG AGA ATC AAG AAA AGC AAG ATG  2165
Ser Asp Asp Glu Pro Lys Arg Ile Lys Lys Ser Lys Met
560              565                 570

ATT GCC AAG GCC TTC TCT AAG CGG CGT GAA CTG CTG CAG  2204
Ile Ala Lys Ala Phe Ser Lys Arg Arg Glu Leu Leu Gln
        575                 580                 585

AAC CCG GGC CAG GAG CTC TCC TTC AGC ATG CAC ACT GTC  2243
Asn Pro Gly Gln Glu Leu Ser Phe Ser Met His Thr Val
                590                 595

TCC CAT GAT GGA CCT GTT GCC GGT TTG GCT TTT GAA CTC  2282
Ser His Asp Gly Pro Val Ala Gly Leu Ala Phe Glu Leu
    600                 605                 610

AAT GAA CCC TCA GCT GAT GTC TCC TCT GCC TGG GCC CAG  2321
Asn Glu Pro Ser Ala Asp Val Ser Ser Ala Trp Ala Gln
            615                 620

CAC GTC ACC AAG ATG GTG GCT CGA AGA GGA GCC ATA TTA  2360
His Val Thr Lys Met Val Ala Arg Arg Gly Ala Ile Leu
625              630                 635

CCC CAG GAT GTG TCT GTC ACC CCT GTG GCA ACT CCA GTG  2399
Pro Gln Asp Val Ser Val Thr Pro Val Ala Thr Pro Val
        640                 645                 650

CCA CCA GAA GAA CAA GCC AAC CTG TGG CTG GTT GAG GCA  2438
Pro Pro Glu Glu Gln Ala Asn Leu Trp Leu Val Glu Ala
                655                 660
```

FIG._1D

```
GAG ATC TCC CCA GAG TTA GAG AAG CGT TTA GGC CGG AAG    2477
Glu Ile Ser Pro Glu Leu Glu Lys Arg Leu Gly Arg Lys
    665             670             675

AAG AAG CGG AGG AAG AGG AAG AAG GAG GTG TGC CCC TTG    2516
Lys Lys Arg Arg Lys Arg Lys Lys Glu Val Cys Pro Leu
            680             685

GGG CCA GCC CCT GAA CTT CAC CAC TCT GCC CCT GTT CCT    2555
Gly Pro Ala Pro Glu Leu His His Ser Ala Pro Val Pro
690             695             700

GCC ACC AGT GCA GTT CCT CGG CTG CCT CAG CTG CCT CGG    2594
Ala Thr Ser Ala Val Pro Arg Leu Pro Gln Leu Pro Arg
        705             710             715

CAG AAG TGC CTA GTA GCT GCA AAT GCC TGG GGA ACA GGA    2633
Gln Lys Cys Leu Val Ala Ala Asn Ala Trp Gly Thr Gly
                720             725

GAG CCC TGC CGA CAG GGA GCC TGG ACT GTA GTC TCC AAC    2672
Glu Pro Cys Arg Gln Gly Ala Trp Thr Val Val Ser Asn
    730             735             740

CCC TTC TGC CCA GAG CCT AGT CCC CAT CAA GAT CCA TTT    2711
Pro Phe Cys Pro Glu Pro Ser Pro His Gln Asp Pro Phe
            745             750

CTC CCT GGT GCC TCA GCC CCC AGG GTC TGG GCT CAG GGC    2750
Leu Pro Gly Ala Ser Ala Pro Arg Val Trp Ala Gln Gly
755             760             765

CGC CTC CAG GGG CTG GGA TCC ATT CAT TCC CGC ACT AAC    2789
Arg Leu Gln Gly Leu Gly Ser Ile His Ser Arg Thr Asn
        770             775             780

CTA ATG GAG GCT GAG CTC TTG GAT GCA GAC TCG GAC TTC TG 2830
Leu Met Glu Ala Glu Leu Leu Asp Ala Asp Ser Asp Phe
                785             790             793

AGCTTGCAGG GCAGGTCCTA GGATGGGGAA GACAAGTGCA CGCCTTCCTA    2880

TAGCTCTTCC TGAGAGCACA CCTCTGGGGT CTCATCTGAC AGTCTATGGG    2930

CCATGTATCT GCCTACAAGA GCTGTGTACG ACTGGCTAGA AGCAGCCAGA    2980

CCATAGAAAC AAGCTGAACA CAGCCACTGA TAGACCTCAC TTCAGAAGCA    3030

AGACCTGCAG TTCAGGACCC TTGCCTCTGC CCCCCAATTA GAGTCTGGCT    3080

GGCAGTGTTA GTCTCCAACA GAGCTTGTAC TAGGGTAGGA ACGGCAGAGG    3130

CAGGGGTGAT GGTACCCAGA GTGGGCTGGG GTGTCCAGTG AGGTAACCAA    3180
```

FIG._1E

```
GCCCATGTCT GGCAGATGAG GGCTGGCTGC CCTTTTCTGT GCCAATGAGT 3230
GCCCTTTTCT GGCGCTCTGA GACCAAAAGT GTTTATTGTG TCATTTGTCC 3280
TTTTTCTAGG TGGGAACAGG ACTCTCTTTT TCCTCTTCCT GGTAGTTGTA 3330
ATGACTACTC CCATAAGGCC TAGAACTGCT CTCAGTAGGT GGCCCTGTCC 3380
AAAACACATC TTCACATCTT AGTTCCACTA GGCCAAACTC TTATTGGTTA 3430
GCACCTTAAA ACACACACAC ACACACACAC ACACACACAC ACACACACAC 3480
ACACACACAC ACCCTCTTAC TTCTGAGCTT GGTCTCAAGA GAGAGACAAC 3530
TGGTTCAGCT CCAGGCCTCT GAGAGTCATG TTTTCTTCCT CACATCCATC 3580
CAGTGGGGAT GGATCCTCTG ACTTAAGGGG CTACCTTGGG AAGCCTCTGT 3630
AGCTTCAGCC AGGCAAGAAA GCTTCTTCCA ACTTCTGTAT CTGGTGGGAA 3680
GGAGGACTCC CTACTTTTTA CAATGTCTAG TCATTTTCAT AGTGCCCCAC 3730
ATTCAAGAAC CAGACAGCAG GATGCCTTAG AAGCTGGCTG GGTTCCAGGT 3780
CAGAGGCTCA GTATGAGAAG AAGAAATATG AACAGTAAAT AAAACATTTT 3830
TGTATAAAAA AAAAAAAAA AAAA 3854
```

FIG._1F

```
rSmo    1    MAAGRPVRGPELAPRRLLQLL.LLVLLGGRGRGAALSGNVTGPGPRSAGG
dSmo    1    MQYLNFPPRMPNIMMFLEVAILCLWVVADASASSAKFGSTTPASAQQSDVE rSmo   50    SARRNAPV.........TSPPPPLLS......HCGRAAHCEPLRY..NVC
dSmo   51    LEPINGTLNYRLYAKKGRDDDKPWFDGLDSRHIQCVRRARCYPTSNATNTC rSmo   83    LGSALPYGATTTLLAGDSDSQEEAHSKLVLWSGLRNAPRCWAVIQPLLCA
dSmo  101    FGSKLPYELSSLDLT.DFHTEKELNDKLNDYYALKHVPKCWAAIQPFLCA rSmo  133    VYMPKCE....NDRVELPSRTLCQATRGPCAIVERERGWPDFLRCTPDHF
dSmo  150    VFKPKCEKINGEDMVYLPSYEMCRITMEPCRHLYNTTFFPKFLRCNETLF rSmo  179    PEGCPNEVQNIKFNSSGQCEAPLVRTDNPKSWYEDVEGCGIQCQNPLFTE
dSmo  200    PTKCTNGARGMKFNGTGQCLSPLVPTDTSASYYPGIEGCGVRCKDPLYTD rSmo  229    AEHQDMHSYIAAFGAWTGLCVLFTLATFVADWRNSNRYPAVILFYVNACF
dSmo  250    DEHRQIHKLHGWAGSICLLSNLFVVSTFFIDWKNANKYPAVIVFYINLCF rSmo  279    FVGSIGWLAQFMDGARREIVCRADGTMRFGEPTSSETLSCVIIFVIVYYA
dSmo  300    LIACVGWLLQFTSGSREDIVCRKDGTLRHSEPTAGENLSCIVIFVLVYYF rSmo  329    LMAGVVWFVVLTYAWHTSFKALGTTYQPLSGKTSYFHLLTWSLPFVLTVA
dSmo  350    LTAGMVWFVFLTYAWH.WRAMGHVQDRIDKKGSYFHLVAWSLPLVLTIT rSmo  379    ILAVAQVDGDSVSGICFVGYKNYRYRAGFVLAPIGLVLTVGGYFQIRGVM
dSmo  398    TMAFSEVDGNSIVGICFVGYINHSMRAGLLLGPLCGVILLGGYFITRGMV rSmo  429    TLFSIKSNHPGLLSEKAASKINETMLRLGTFGFVLITFSCHFYDF
dSmo  448    MLFGLKHFANDIKSTSASNKIHLIMRMGVCALLTLVFILVAIACHVTEF
```

*FIG._2A*

```
rSmo  479  FNQAEWERSFRDYVLCQANVTIGLPTKKPIPDCEIKNRPSLLVEKINLFA
dSmo  498  RHADEWAQSFRQFIIC..KISSVFEEK...SSCRIENRPSVGVLQLHLLC rSmo  529  MFGTGIAMSTWVWTKATLLIWRRTWCRLTGHSDDEPKRIKKSKMIAKAFS
dSmo  543  LFSSGIVMSTWCWTPSSIETWKRRYIRKKCGKEVVEEVKMPKHKVIAQTWA rSmo  579  KRRELLQNPGQELSFSMHTVSHDGPVAGLAFELNE....PSADVSSAWAQ
dSmo  593  KRKD.FEDKGR.LSITLYN.THTDPV.GLNFDVNDLNSSETNDISSTWAA rSmo  625  HVTKMVARR....GAILPQDVSVTPVATPVPPEEQANLWL.....VE
dSmo  639  YLPQCVKRRMALTGAATGNSSSHGPRKNSLDSEISVSVRHVSVESRRNSV rSmo  663  AEISPELEKRLGRKKKRRKKEVCPLGPAPELHHSAPVPATSAVPRLPQ
dSmo  689  DSQVSVKIAEMKTKVASRSRGKHGGSSNRRTQRRRDYIAAAT..GKSSR rSmo  713  LPRQKCLVAANAWGTGEPCRQGAWTVVSNPFCPEPSPHQDPFLPGASAPR
dSmo  737  RRESSTSVESQVIALKKTTYPNASHKVGVFAHHSSKKQHNYTSSMKRRTA rSmo  763  VWAQGRLQGLGSIHSRTNLMEAELLDADSDF
dSmo  787  NAGLDPSILNEFLQKNGDFIFPFLQNQDMSSSSEEDNSRASQKIQDLNVV dSmo  837  VKQQEISEDDHDGIKIEELPNSKQVALENFLKNIKKSNESNSNRHSRNSA dSmo  887  RSQSKKSQKRHLKNPAADLDFRKDCVKYRSNDSLSCSSEELDVALDVGSL dSmo  937  LNSSFSGISMGKPHSRNSKTSCDVGIQANPFELVPSYGEDELQQAMRLLN dSmo  987  AASRQRTEAANEDFGGTELQGLLGHSHRHQREPTFMSESDKLKMLLPSK
```

FIG._2B

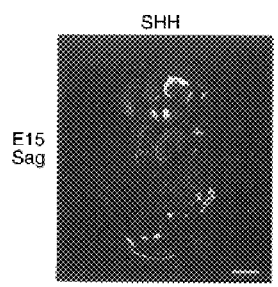
FIG._3A
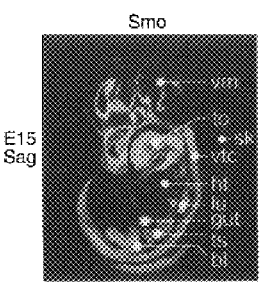
FIG._3B
FIG._3C
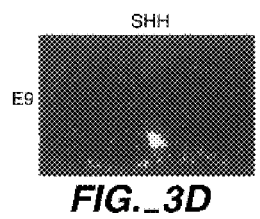
FIG._3D
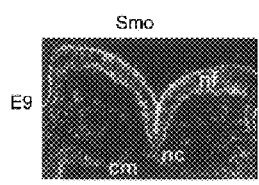
FIG._3E
FIG._3F
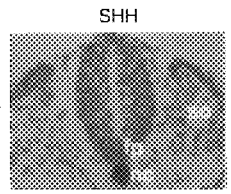
FIG._3G
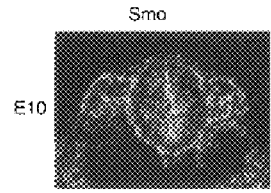
FIG._3H
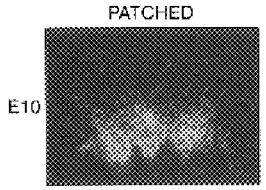
FIG._3I

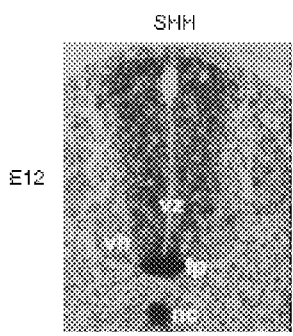
FIG._3J
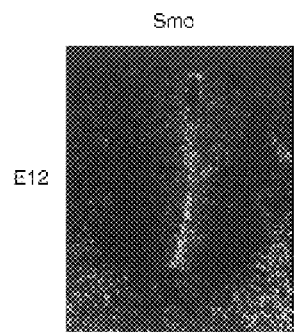
FIG._3K
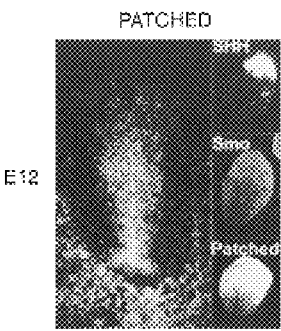
FIG._3L
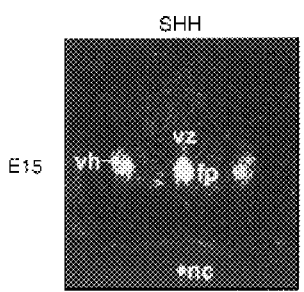
FIG._3M
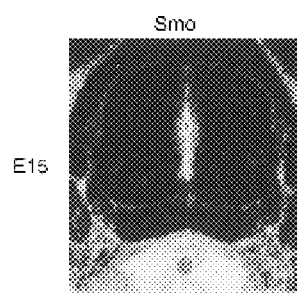
FIG._3N
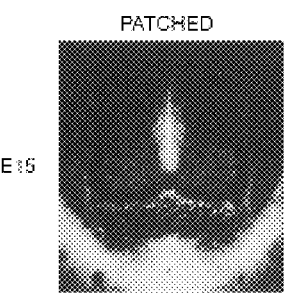
FIG._3O

| | | | | | |
|---|---|---|---|---|---|
| 1 | CGGGGGTTGG | CCATGGCCGC | TGCCCGCCCA | GCGCGGGGGC | CGGAGCTCCC |
| 1 | | MetAlaAl Met | aAlaArgPro | AlaArgGlyP | roGluLeuPr |
| 51 | GCTCCTGGGG | CTGCTGCTGC | TGCTGCTGCT | GGGGGACCCG | GGCCGGGGGG |
| 14 | oLeuLeuGly | LeuLeuLeuL | euLeuLeuLe | uGlyAspPro | GlyArgGlyAla |
| 101 | CGGCCTCGAG | CGGGAACGCG | ACCGGGCCTG | GCCTCGGAG | CGCGGGCGGG |
| 31 | AlaSerSe | rGlyAsnAla | ThrGlyProG | lyProArgSe | rAlaGlyGly |
| 151 | AGCGCGAGGA | GGAGCGCGGC | GGTGACTGGC | CCTCCGCCGC | CGCTGAGCCA |
| 47 | SerAlaArgA | rgSerAlaAl | aValThrGly | ProProProP | roLeuSerHis |
| 201 | CTGCGGCCGG | GCTGCCCCT | GCGAGCCGCT | GCGCTACAAC | GTGTGCCTGG |
| 64 | CysGlyArg | AlaAlaProC | ysGluProLe | uArgTyrAsn | ValCysLeuG |
| 251 | GCTCGGTGCT | GCCCTACGGG | CCACCTCCA | CACTGCTGGC | CGGAGACTCG |
| 81 | lySerValLe | uProTyrGly | AlaThrSerT | hrLeuLeuAl | aGlyAspSer |
| 301 | GACTCCCAGG | AGGAAGCGCA | CGGCAAGCTC | GTGCTCTGGT | CGGGCCTCCG |
| 97 | AspSerGlnG | luGluAlaHi | sGlyLysLeu | ValLeuTrpS | erGlyLeuAr |
| 351 | GAATGCCCCC | CGCTGCTGGG | CAGTGATCCA | GCCCTGCTG | TGTGCCGTAT |
| 114 | gAsnAlaPro | ArgCysTrpA | laValIleGl | nProLeuLeu | CysAlaValTyr |
| 401 | ACATGCCCAA | GTGTGAGAAT | GACCGGGTGG | AGCTGCCCAG | CCGTACCCTC |
| 131 | MetProLy | sCysGluAsn | AspArgValG | luLeuProSe | rArgThrLeu |
| 451 | TGCCAGGCCA | CCCGAGGCCC | CTGTGCCATC | GTGGAGAGGG | AGCGGGGCTG |
| 147 | CysGlnAlaT | hrArgGlyPr | oCysAlaIle | ValGluArgG | luArgGlyTrp |
| 501 | GCCTGACTTC | CTGCGCTGCA | CTCCTGACCG | CTTCCCTGAA | GGCTGCACGA |
| 164 | ProAspPhe | LeuArgCysT | hrProAspAr | gPheProGlu | GlyCysThrA |
| 551 | ATGAGGTGCA | GAACATCAAG | TTCAACAGTT | CAGGCCAGTG | CGAAGTGCCC |
| 181 | snGluValGl | nAsnIleLys | PheAsnSerS | erGlyGlnCy | sGluValPro |
| 601 | TTGGTTCGGA | CAGACAACCC | CAAGAGCTGG | TACGAGGACG | TGGAGGGCTG |
| 197 | LeuValArgT | hrAspAsnPr | oLysSerTrp | TyrGluAspV | alGluGlyCy |

FIG._4A

```
 651  CGGCATCCAG TGCCAGAACC CGCTCTTCAC AGAGGCTGAG CACCAGGACA
 214   sGlyIleGln CysGlnAsnP roLeuPheTh rGluAlaGlu HisGlnAspMet
 701  TGCACAGCTA CATCGCGGCC TTCGGGGCCG TCACGGGCCT CTGCACGCTC
 231     HisSerTy rIleAlaAla PheGlyAlaV alThrGlyLe uCysThrLeu
 751  TTCACCCTGG CCACATTCGT GGCTGACTGG CGGAACTCGA ATCGCTACCC
 247   PheThrLeuA laThrPheVa lAlaAspTrp ArgAsnSerA snArgTyrPro
 801  TGCTGTTATT CTCTTCTACG TCAATGCGTG CTTCTTTGTG GGCAGCATTG
 264     AlaValIle LeuPheTyrV alAsnAlaCy sPhePheVal GlySerIleG
                                                   start clone 14
 851  GCTGGCTGGC CCAGTTCATG GATGGTGCCC GCCGAGAGAT CGTCTGCCGT
 281   lyTrpLeuAl aGlnPheMet AspGlyAlaA rgArgGluIl eValCysArg
 901  GCAGATGGCA CCATGAGGCT GGGGAGCCC ACCTCCAATG AGACTCTGTC
 297   AlaAspGlyT hrMetArgLe uGlyGluPro ThrSerAsnG luThrLeuSe
 951  CTGCGTCATC ATCTTTGTCA TCGTGTACTA CGCCCTGATG GCTGGTGTGG
 314   rCysValIle IlePheValI leValTyrTy rAlaLeuMet AlaGlyValVal
1001  TTTGGTTTGT GGTCCTCACC TATGCCTGGC ACACTTCCTT CAAAGCCCTG
 331     TrpPheVa lValLeuThr TyrAlaTrpH isThrSerPh eLysAlaLeu
1051  GGCACCACCT ACCAGCCTCT CTCGGGCAAG ACCTCCTACT TCCACCTGCT
 347   GlyThrThrT yrGlnProLe uSerGlyLys ThrSerTyrP heHisLeuLeu
1101  CACCTGGTCA CTCCCCTTTG TCCTCACTGT GGCAATCCTT GCTGTGGCGC
 364     ThrTrpSer LeuProPheV alLeuThrVa lAlaIleLeu AlaValAlaG
1151  AGGTGGATGG GGACTCTGTG AGTGGCATTT GTTTTGTGGG CTACAAGAAC
 381   lnValAspGl yAspSerVal SerGlyIleC ysPheValGl yTyrLysAsn
1201  TACCGATACC GTGCGGGCTT CGTGCTGGCC CCAATCGGCC TGGTGCTCAT
 397   TyrArgTyrA rgAlaGlyPh eValLeuAla ProIleGlyL euValLeuIl
1251  CGTGGGAGGC TACTTCCTCA TCCGAGGAGT CATGACTCTG TTCTCCATCA
 414   eValGlyGly TyrPheLeuI leArgGlyVa lMetThrLeu PheSerIleLys
```

FIG._4B

```
1301    AGAGCAACCA  CCCCGGGCTG  CTGAGTGAGA  AGGCTGCCAG  CAAGATCAAC
 431      SerAsnHi  sProGlyLeu  LeuSerGluL  ysAlaAlaSe  rLysIleAsn

1351    GAGACCATGC  TGCGCCTGGG  CATTTTTGGC  TTCCTGGCCT  TTGGCTTTGT
 447     GluThrMetL  euArgLeuGl  yIlePheGly  PheLeuAlaP  heGlyPheVal

1401    GCTCATTACC  TTCAGCTGCC  ACTTCTACGA  CTTCTTCAAC  CAGGCTGAGT
 464      LeuIleThr  PheSerCysH  isPheTyrAs  pPhePheAsn  GlnAlaGluT

1451    GGGAGCGCAG  CTTCCGGGAC  TATGTGCTAT  GTCAGGCCAA  TGTGACCATC
 481     rpGluArgSe  rPheArgAsp  TyrValLeuC  ysGlnAlaAs  nValThrIle

1501    GGGCTGCCCA  CCAAGCAGCC  CATCCCTGAC  TGTGAGATCA  AGAATCGCCC
 497     GlyLeuProT  hrLysGlnPr  oIleProAsp  CysGluIleL  ysAsnArgPr

1551    GAGCCTTCTG  GTGGAGAAGA  TCAACCTGTT  TGCCATGTTT  GGAACTGGCA
 514     oSerLeuLeu  ValGluLysI  leAsnLeuPh  eAlaMetPhe  GlyThrGlyI

1601    TCGCCATGAG  CACCTGGGTC  TGGACCAAGG  CCACGCTGCT  CATCTGGAGG
 531       AlaMetSe  rThrTrpVal  TrpThrLysA  laThrLeuLe  uIleTrpArg

1651    CGTACCTGGT  GCAGGTTGAC  TGGGCAGAGT  GACGATGAGC  CAAAGCGGAT
 547     ArgThrTrpC  ysArgLeuTh  rGlyGlnSer  AspAspGluP  roLysArgIle

1701    CAAGAAGAGC  AAGATGATTG  CCAAGGCCTT  CTCTAAGCGG  CACGAGCTCC
 564      LysLysSer  LysMetIleA  laLysAlaPh  eSerLysArg  HisGluLeuL

1751    TGCAGAACCC  AGGCCAGGAG  CTGTCCTTCA  GCATGCACAC  TGTGTCCCAC
 581     euGlnAsnPr  oGlyGlnGlu  LeuSerPheS  erMetHisTh  rValSerHis

1801    GACGGGCCCG  TGGCGGGCTT  GGCCTTTGAC  CTCAATGAGC  CCTCAGCTGA
 597     AspGlyProV  alAlaGlyLe  uAlaPheAsp  LeuAsnGluP  roSerAlaAs

1851    TGTCTCCTCT  GCCTGGGCCC  AGCATGTCAC  CAAGATGGTG  GCTCGGAGAG
 614     pValSerSer  AlaTrpAlaG  lnHisValTh  rLysMetVal  AlaArgArgGly
                                end clone 5

1901    GAGCCATACT  GCCCCAGGAT  ATTTCTGTCA  CCCCTGTGGC  AACTCCAGTG
 631      AlaIleLe   uProGlnAsp  IleSerValT  hrProValAl  aThrProVal
```

*FIG._4C*

```
1951  CCCCCAGAGG AACAAGCCAA CCTGTGGCTG GTTGAGGCAG AGATCTCCCC
 647  ProProGluG luGlnAlaAs nLeuTrpLeu ValGluAlaG luIleSerPro
2001  AGAGCTGCAG AAGCGCCTGG GCCGGAAGAA GAAGAGGAGG AAGAGGAAGA
 664     GluLeuGln LysArgLeuG lyArgLysLy sLysArgArg LysArgLysL
2051  AGGAGGTGTG CCCGCTGGCG CCGCCCCTG AGCTTCACCC CCCTGCCCCT
 681  ysGluValCy sProLeuAla ProProProG luLeuHisPr oProAlaPro
2101  GCCCCAGTA CCATTCCTCG ACTGCCTCAG CTGCCCCGGC AGAAATGCCT
 697  AlaProSerT hrIleProAr gLeuProGln LeuProArgG lnLysCysLe
2151  GGTGGCTGCA GGTGCCTGGG GAGCTGGGGA CTCTTGCCGA CAGGGAGCGT
 714  uValAlaAla GlyAlaTrpG lyAlaGlyAs pSerCysArg GlnGlyAlaTrp
2201  GGACCCTGGT CTCCAACCCA TTCTGCCCAG AGCCCAGTCC CCCTCAGGAT
 731     ThrLeuVa lSerAsnPro PheCysProG luProSerPr oProGlnAsp
2251  CCATTTCTGC CCAGTGCACC GGCCCCGTG GCATGGGCTC ATGGCCGCCG
 747  ProPheLeuP roSerAlaPr oAlaProVal AlaTrpAlaH isGlyArgArg
2301  ACAGGGCCTG GGGCCTATTC ACTCCCGCAC CAACCTGATG GACACAGAAC
 764     GlnGlyLeu GlyProIleH isSerArgTh rAsnLeuMet AspThrGluL
2351  TCATGGATGC AGACTCGGAC TTCTGAGCCT GCAGAGCAGG ACCTGGGACA
 781  euMetAspAl aAspSerAsp Phe
                              Stop
2401  GGAAAGAGAG GAACCAATAC CTTCAAGGCT CTTCTTCCTC ACCGAGCATG

2451  CTTCCCTAGG ATCCGTCTT CCAGAGAACC TGTGGGCTGA CTGCCCTCCG

2501  AAGAGAGTTC TGGATGTCTG GCTCAAAGCA GCAGGACTGT GGGAAAGAGC

2551  CTAACATCTC CATGGGGAGG CCTCACCCCA GGGACAGGGC CCTGGAGCTC

2601  AGGGTCCTTG TTTCTGCCCT GCCAGCTGCA GCCTGGTTGG CAGCATCTGC
```

FIG._4D

```
2651    TCCATCGGGG CAGGGGGTAT GCAGAGCTTG TGGTGGGGCA GGAACGGTGG

2701    AGGCAGAGGT GACAGTTCCC AGAGTGGGCT TTGGTGGCCA GGGAGGCAGC

2751    CTAGCCTATG TCTGGCAGAT GAGGGCTGGC TGCCGTTTTC TGGGCTGATG

2801    GGTGCCCTTT CCTGGCAGTC TCAGTCCAAA AGTGTTGACT GTGTCATTAG

2851    TCCTTTGTCT AAGTAGGGCC AGGGCACCGT ATTCCTCTCC CAGGTGTTTG

2901    TGGGGCTGGA AGGACCTGCT CCCACAGGGG CCATGTCCTC TCTTAATAGG

2951    TGGCACTACC CCAAACCCAC CG
```

FIG._4E

```
hSmo     1   . . . . . . . . . . . . . . . . . . . . . . . . . M A A A R P A R G P E . . . . . . . . . . . . . . . L P . . . . . . . . . L L G L L L L L L L G . .
rat.smo  1   . . . . . . . . . . . . . . . . . . . . . . . . . M A A G R P V R G P E . . . . . . . . . . . . . . L A P R R L L Q L L L L V L L G . .
dros.smo 1   M H X R T A E Q E T G I Q P I K I H T R Q L F N D F Y K R M Q Y L N F P R M P N I M M F L E V A I L hSmo     25  . . . D P G R G A A S S G N A T G P G P R S A G G S A R R S A A V T G P . . . . . . . . . . . . . . . . . . . . . . . . . P P
rat.smo  28  . . . G R G R G A A L S G N V T G P G P R S A G G S A R R N A P V T S P . . . . . . . . . . . . . . . . . . . . . . . . . P P
dros.smo 51  C L W V V A D A S A S S A K F G S T T P A S A Q Q S D V E L E P I N G T L N Y R L Y A K K G R D D K hSmo     60  P . L S . . . . . . H C G R A A P C E P L R Y . . N V C L G S V L P Y G A T S T L L A G D S D S Q
rat.smo  63  P L L S . . . . . . H C G R A A H C E P L R Y . . N V C L G S A L P Y G A T T T L L A G D S D S Q
dros.smo 101 P W F D G L D S R H I Q C V R R A R C Y P T S N A T N T C F G S K L P Y E L S S L D L T . D F H T E hSmo     100 E E A H G K L V L W S G L R N A P R C W A V I Q P L L C A V Y M P K C E . . . . . . N D R V E L P S R T
rat.smo  104 E E A H S K L V L W S G L R N A P R C W A V I Q P L L C A V Y M P K C E . . . . . . N D R V E L P S R T
dros.smo 150 K E L N D K L N D Y Y A L K H V P K C W A I Q P F L C A V F K P K C E K I N G E D M V Y L P S Y E hSmo     146 L C Q A T R G P C A I V E R E R G W P D F L R C T P D R F P E G C T N E V Q N I K F N S S G Q C E V
rat.smo  150 L C Q A T R G P C A I V E R E R G W P D F L R C T P D H F P E G C T N E V Q N I K F N S S G Q C E A
dros.smo 200 M C R I T M E P C R L Y N T T F F P K F L R C N E T L F P T K C T N G A R G M K F N G T G Q C L S
```

FIG._5A

| | | |
|---|---|---|
| hSmo | 196 | PLVRTDNPKSWYEDVEGCGIQCQNPLFTEAEHQDMHSYIAAFGAVTGLCT |
| rat.smo | 200 | PLVRTDNPKSWYEDVEGCGIQCQNPLFTEAEHQDMHSYIAAFGAVTGLCT |
| dros.smo | 250 | PLVPTDTSASYYPGIEGCGVRCKDPLYTDDEHRQIHKLIGWAGSICLLSN |

| | | |
|---|---|---|
| hSmo | 246 | LFTLATFVADWRNSNRYPAVILFYVNACFFVGSIGWLAQFMDGARREIVC |
| rat.smo | 250 | LFTLATFVADWRNSNRYPAVILFYVNACFFVGSIGWLAQFMDGARREIVC |
| dros.smo | 300 | LFVVSTFFIDWKNANKYPAVIVFYINLCFLIACVGWLLQFTSGSREDIVC |

| | | |
|---|---|---|
| hSmo | 296 | RADGTMRLGEPTSNETLSCVIIFVIVYYALMAGVVWFVVLTYAWHTSFKA |
| rat.smo | 300 | RADGTMRFGEPTSSETLSCVIIFVIVYYALMAGVVWFVVLTYAWHTSFKA |
| dros.smo | 350 | RKDGTLRHSEPTAGENLSCIVIFVLVYYFLTAGMVWFVFLTYAWH--WRA |

| | | |
|---|---|---|
| hSmo | 346 | LGTTYQPLSGKTSYFHLLTWSLPFVLTVAILAVAQVDGDSVSGICFVGYK |
| rat.smo | 350 | LGTTYQPLSGKTSYFHLLTWSLPFVLTVAILAVAQVDGDSVSGICFVGYK |
| dros.smo | 398 | MGHVQDRIDKKGSYFHLVAWSLPLVLTITTMAFSEVDGNSIVGICFVGYI |

| | | |
|---|---|---|
| hSmo | 396 | NYRYRAGFVLAPIGLVLIVGGYFLIRGVMTLFSIKSNHPGLLSEKAASKI |
| rat.smo | 400 | NYRYRAGFVLAPIGLVLIVGGYFLIRGVMTLFSIKSNHPGLLSEKAASKI |
| dros.smo | 448 | NHSMRAGLLLGPLCGVILIGGYFITRGMVMLFGLKHFANDIKSTSASNKI |

FIG._5B

| | | |
|---|---|---|
| hSmo | 446 | N E T M L R L G I F G F L A F G F V L I T F S C H F Y D F F N Q A E W E R S F R D Y V L C Q A N V T |
| rat.smo | 450 | N E T M L R L G I F G F L A F G F V L I T F S C H F Y D F F N Q A E W E R S F R D Y V L C Q A N V T |
| dros.smo | 498 | H L I I M R M G V C A L L T L V F I L V A I A C H V T E F R H A D E W A Q S F R Q F I I C . . K I S |
| | | |
| hSmo | 496 | I G L P T K Q P I P D C E I K N R P S L L V E K I N L F A M F G T G I A M S T W V W T K A T L L I W |
| rat.smo | 500 | I G L P T K K P I P D C E I K N R P S L L V E K I N L F A M F G T G I A M S T W V W T K A T L L I W |
| dros.smo | 546 | S V F E E K . . . S S C R I E N R P S V G V L Q L H L C L F S S G I V M S T W C W T P S S I E T W |
| | | |
| hSmo | 546 | R R T W C R L T G Q S D D E P K R I K K S K M I A K A F S K R H E L L Q N P G Q E L S F S M H T V S |
| rat.smo | 550 | R R T W C R L T G H S D D E P K R I K K S K M I A K A F S K R R E L L Q N P G Q E L S F S M H T V S |
| dros.smo | 593 | K R Y I R K K C G K E V V E E V K M P K H K V L A Q T W A K R K D . F E D K G R . L S I T L Y N . T |
| | | |
| hSmo | 596 | H D G P V A G L A F D L N E . . . . . . P S A D V S S A W A Q H V T K M V A R R . . . . . . . . . . G A I L P Q D I |
| rat.smo | 600 | H D G P V A G L A F E L N E . . . . . . P S A D V S S A W A Q H V T K M V A R R . . . . . . . . . . G A I L P Q D V |
| dros.smo | 640 | H T D P V . G L N F D V N D L N S S E T N D I S S T W A A Y L P Q C V K R R M A L T G A A T G N S S |
| | | |
| hSmo | 638 | S V T P V A T P V P P E E Q A N L W L . . . . . V E A E I S . . . P E L Q K R L G . . . . . . . . |
| rat.smo | 642 | S V T P V A T P V P P E E Q A N L W L . . . . . V E A E I S . . . P E L E K R L G . . . . . . . . |
| dros.smo | 689 | S H G P R K N S L D S E I S V S V R H V S V E S R R N S V D S Q V S V K I A E M K T K V A S R S R G |

FIG._5C

```
hSmo     671  . . . . . . . . . . . . . . . . . . . . . . . . . . . . . . . . . . . . . . . . . . .
rat.smo  675  . . . . . . . . . . . . . . . . . . . . . . . . . . . . . . . . . . . . . . . . . . .
dros.smo 739  K H G G S S S N R R T Q R R R K R R D Y I A A A T G K S S R R E S S T S V E S Q V I A L K K T T Y P N A hSmo     682  . . . . . . . . . . . . . . . . . . . . . . . . . . . . . . . . V C P L . . . . . . . . .
rat.smo  686  . . . . . . . . . . . . . . . . . . . . . . . . . . . . . . . . V C P L . . . . . . . . .
dros.smo 789  S H K V G V F A H H S S K K Q H N Y T S S M K R R T A N A G L D P S I L N E F L Q K N G D F I F P F hSmo     686  . . . . . . . . . A P P E L H P P A P A P S T . . I P R L P Q L . . . . . . . . . . . . . P R
rat.smo  690  . . . . . . . . . G P A P E L H H S A P V P A T S A V P R L P Q L . . . . . . . . . . . . . P R
dros.smo 839  L Q N Q D M S S S E E D N S R A S Q K I Q D L N V V V K Q Q E I S E D D H D G I K I E E L P N S K hSmo     710  . . Q . . . . . . . . . . . . . . . . . K C L V A A G A W G A G D S C R Q G A W . . . . . . .
rat.smo  716  . . Q . . . . . . . . . . . . . . . . . K C L V A A N A W G T G E P C R Q G A W . . . . . . .
dros.smo 889  Q V A L E N F L K N I K K S N E S N S N R H S R N S A R S Q S K K S Q K R H L K N P A A D L Q F R K
```

FIG._5D

```
hSmo      731  . . . . . . . . . . . . . . . . . . . . . . . . . . . . . . . . . . . . . . . T L V S N P F C P . . . . . . . . . . . . . . . . . . . . . . . . . . . . .                           E
rat.smo   737  . . . . . . . . . . . . . . . . . . . . . . . . . . . . . . . . . . . . . . . T V S N P F C P . . . . . . . . . . . . . . . . . . . . . . . . . . . . .                           E
dros.smo  939  D C V K Y R S N D S L S C S S E E L D V A L D V G S L L N S S F S G I S M G K P H S R N S K T S C D hSmo      741  P S P P Q D P F . . . L P S . . . . . . . . . . . . . . . . . A P A P V A W A H G R R Q G L G P . .
rat.smo   747  P S P H Q D P F . . . L P G . . . . . . . . . . . . . . . . . A S A P R V W A Q G R L Q G L G S I . .
dros.smo  989  V G I Q A N P F E L V P S Y G E D E L Q Q A M R L L N A A S R Q R T E A A N E O F G G T E L Q G L L hSmo      770  . H S R T N L M D T E L M Q D A D S D F . . . . . . . . . . . . . . . . . . . . . . . . . . . . . .
rat.smo   776  . H S R T N L M E A E L L D A D S D F . . . . . . . . . . . . . . . . . . . . . . . . . . . . . .
dros.smo  1039 G H S H R H Q R E P T F M S E S D K L K M L L P S K
```

*FIG._5E*

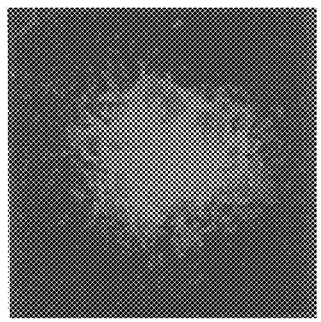
*FIG._6A*
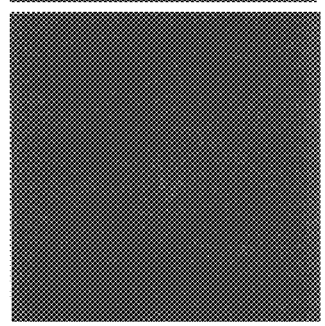
*FIG._6B*
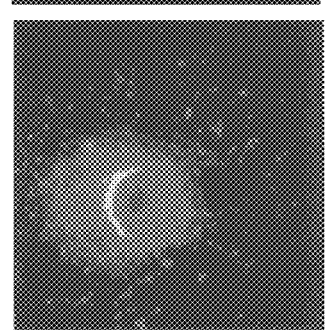
*FIG._6C*
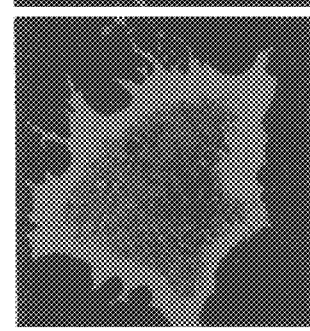
*FIG._6D*
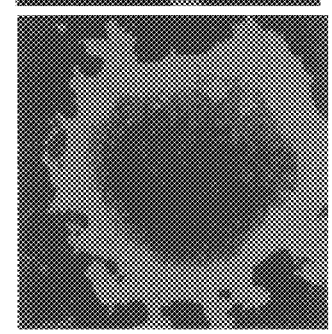
*FIG._6E*
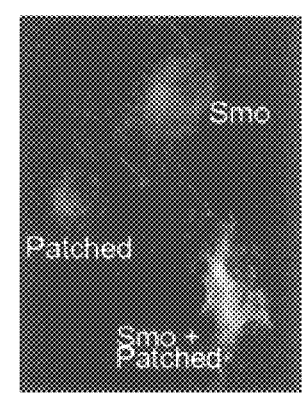
*FIG._7A*

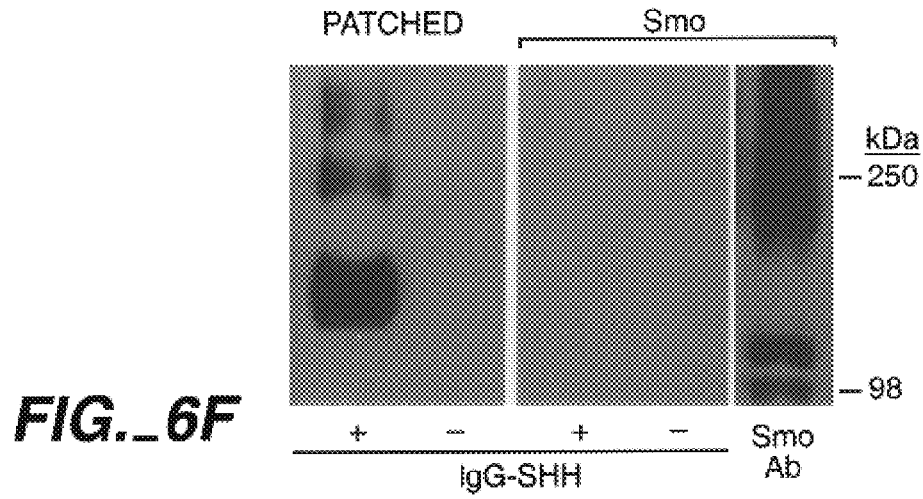
FIG._6F
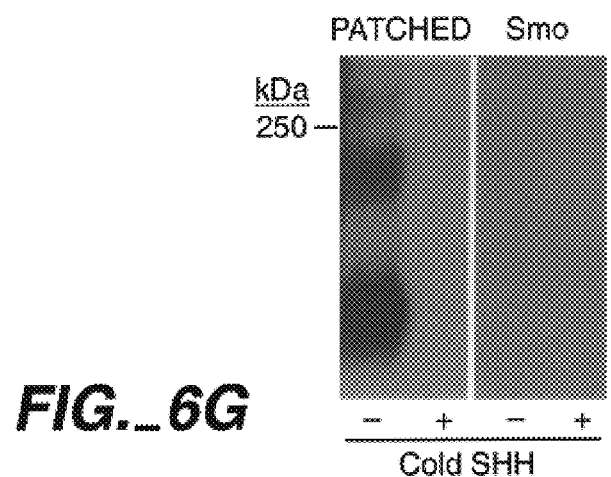
FIG._6G
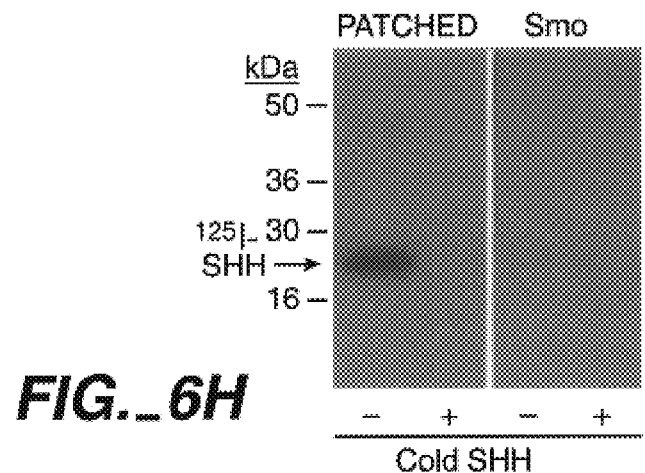
FIG._6H

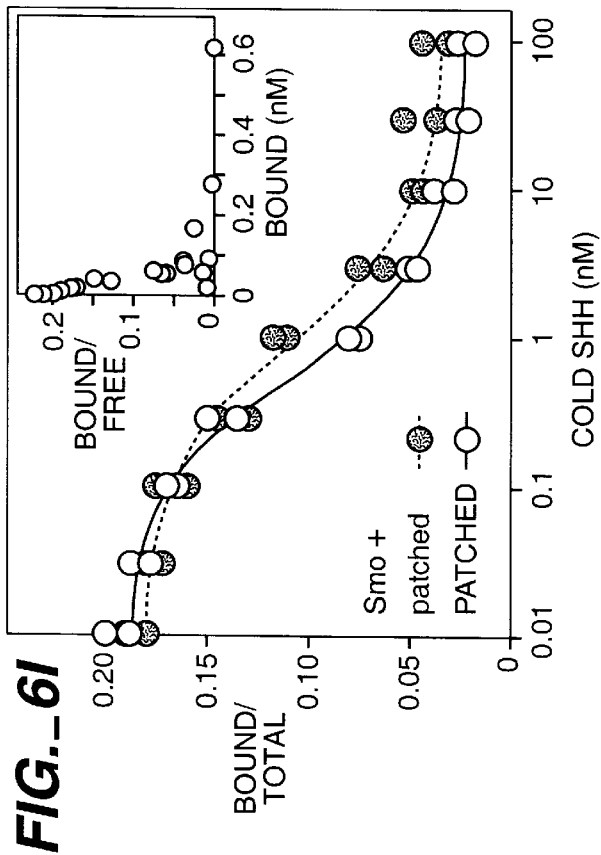
FIG._6I
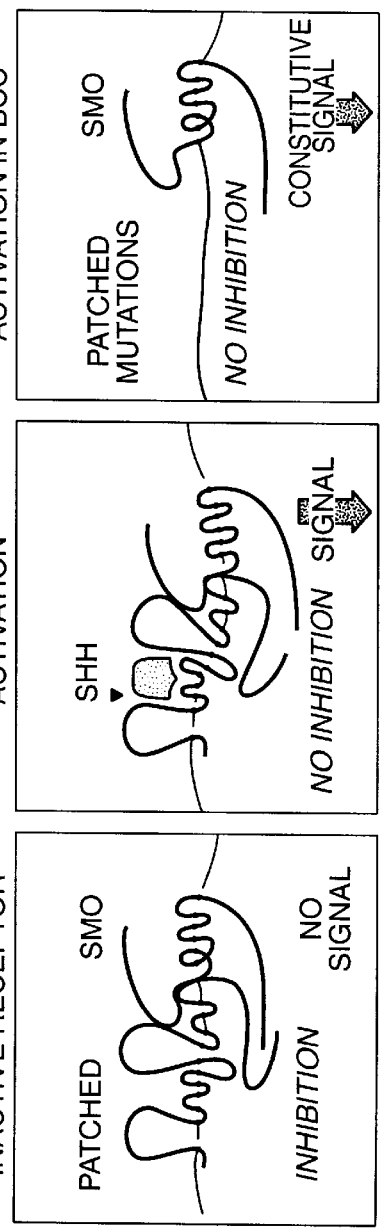
FIG._9

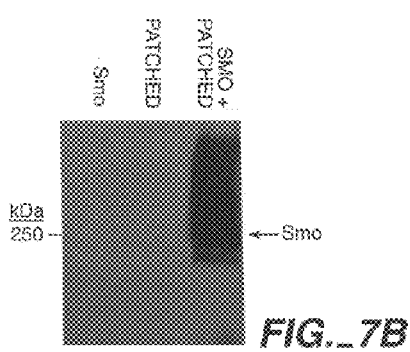
*FIG._7B*
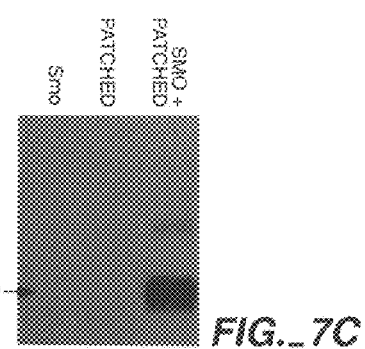
*FIG._7C*
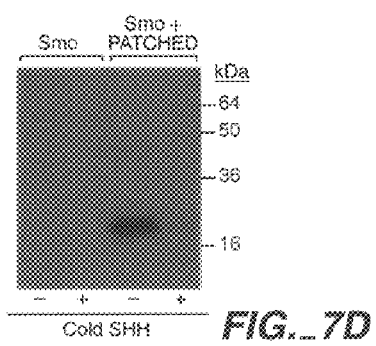
*FIG._7D*
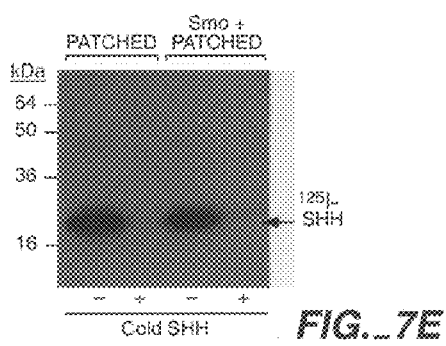
*FIG._7E*
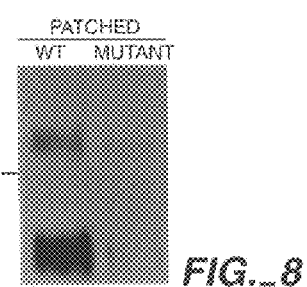
*FIG._8*

6,136,958

ANTIBODIES TO VERTEBRATE SMOOTHENED PROTEINS

RELATED APPLICATION

This application is a non-provisional application filed under 37 CFR 1.53(b)(1), claiming priority under 35 USC 119(e) to provisional application Ser. No. 60/027,070 filed Sep. 30, 1996, the contents of which are incorporated herein by reference.

FIELD OF THE INVENTION

The present invention relates generally to novel Smoothened proteins which interact with Hedgehog and Patched signalling molecules involved in cell proliferation and differentiation. In particular, the invention relates to newly identified and isolated vertebrate Smoothened proteins and DNA encoding the same, including rat and human Smoothened, and to various modified forms of these proteins, to vertebrate Smoothened antibodies, and to various uses thereof.

BACKGROUND OF THE INVENTION

Development of multicellular organisms depends, at least in part, on mechanisms which specify, direct or maintain positional information to pattern cells, tissues, or organs. Various secreted signalling molecules, such as members of the transforming growth factor-beta ("TGF-beta"), Wnt, fibroblast growth factor ("FGF"), and hedgehog families, have been associated with patterning activity of different cells and structures in Drosophila as well as in vertebrates [Perrimon, *Cell*, 80:517–520 (1995)].

Studies of Drosophila embryos have revealed that, at cellular blastoderm and later stages of development, information is maintained across cell borders by signal transduction pathways. Such pathways are believed to be initiated by extracellular signals like Wingless ("Wg") and Hedgehog ("Hh"). The extracellular signal, Hh, has been shown to control expression of TGF-beta, Wnt and FGF signalling molecules, and initiate both short-range and long-range signalling actions. A short-range action of Hh in Drosophila, for example, is found in the ventral epidermis, where Hh is associated with causing adjacent cells to maintain wingless (wg) expression [Perrimon, *Cell*, 76:781–784 (1994)]. In the vertebrate central nervous system, for example, Sonic hedgehog ("SHh"; a secreted vertebrate homologue of dHh) is expressed in notocord cells and is associated with inducing floor plate formation within the adjacent neural tube in a contact-dependent manner [Roelink et al., *Cell*, 76:761–775 (1994)]. Perrimon, *Cell*, 80:517–520 (1995) provide a general review of some of the long-range actions associated with Hh.

Studies of the Hh protein in Drosophila ("dHh") have shown that hh encodes a 46 kDa native protein that is cleaved into a 39 kDa form following signal sequence cleavage and subsequently cleaved into a 19 kDa amino-terminal form and a 26 kDa carboxy-terminal form [Lee et al., *Science*, 2:1528–1537 (1994)]. Lee et al. report that the 19 kDa and 26 kDa forms have different biochemical properties and are differentially distributed. DiNardo et al. and others have disclosed that the dHh protein triggers a signal transduction cascade that activates wg [DiNardo et al., *Nature*, 3:604–609 (1988); Hidalgo and Ingham, *Development*, 110:291–301 (1990); Ingham and Hidalgo, *Development*, 117:283–291 (1993)] and at least another segment polarity gene, patched (ptc) [Hidalgo and Ingham, supra; Tabata and Kornberg, *Cell*, 76:89–102 (1994)]. Properties and characteristics of dHh are also described in reviews by Ingham et al., *Curr. Opin. Genet. Dev.*, 5:492–498 (1995) and Lumsden and Graham et al., *Curr. Biol.*, 5:1347–1350 (1995). Properties and characteristics of the vertebrate homologue of dHh, Sonic hedgehog, are described by Echelard et al., *Cell*, 75:1417–1430 (1993); Krauss et al., *Cell*, 75:1431–1444 (1993); Riddle et al., *Cell*, 75:1401–1416 (1993); Johnson et al., *Cell*, 79:1165–1173 (1994); Fan et al., *Cell*, 81:457–465 (1995); Roberts et al., *Development*, 121:3163–3174 (1995); and Hynes et al., *Cell*, 80:95–101 (1995).

In Perrimon, *Cell*, 80:517–520 (1995), it was reported that the biochemical mechanisms and receptors by which signalling molecules like Wg and Hh regulate the activities, transcription, or both, of secondary signal transducers have generally not been well understood. In Drosophila, genetic evidence indicates that Frizzled ("Fz") functions to transmit and transduce polarity signals in epidermal cells during hair and bristle development. Fz rat homologues which have structural similarity with members of the G-protein-coupled receptor superfamily have been described by Chan et al., *J. Biol. Chem.*, 267:25202–25207 (1992). Specifically, Chan et al. describe isolating two different cDNAs from a rat cell library, the first cDNA encoding a predicted 641 residue protein, is Fz-1, having 46% homology with Drosophila Fz, and a second cDNA encoding a protein, Fz-2, of 570 amino acids that is 80% homologous with Fz-1. Chan et al. state that mammalian fz may constitute a gene family important for transduction and intercellular transmission of polarity information during tissue morphogenesis or in differentiated tissues. Recently, Bhanot et al. did describe the identification of a Drosophila gene, frizzled2 (Dfz2), and predicted Dfz2 protein, which can function as a Wg receptor in cultured cells [Bhanot et al., *Nature*, 382:225–230 (1996)]. Bhanot et al. disclose, however, that there is no in vivo evidence that shows Dfz2 is required for Wg signalling.

Although some evidence suggests that cellular responses to dHh are dependent on the transmembrane protein, smoothened (dSmo), [Nusslein-Volhard et al., *Wilhelm Roux's Arch. Dev. Biol.*, 193:267–282 (1984); Jurgens et al., *Wilhem Roux's Arch. Dev. Biol.*, 193:283–295 (1984); Alcedo et al., *Cell*, 86:221–232 (Jul. 26, 1996); van den Heuvel and Ingham, *Nature*, 382:547–551 (Aug. 8, 1996)], and are negatively regulated by the transmembrane protein, "Patched" [(Hooper and Scott, *Cell*, 5:751–765 (1989); Nakano et al., *Nature*, 341:508–513 (1989); Hidalgo and Ingham, supra; Ingham et al., *Nature*, 353:184–187 (1991)], the receptors for Hh proteins have not previously been biochemically characterized. Various gene products, including the Patched protein, the transcription factor cubitus interruptus, the serine/threonine kinase "fused", and the gene products of Costal-2, smoothened (smo) and Suppressor of fused (Su(fu)), have been implicated as putative components of the Hh signalling pathway.

Prior studies in Drosophila led to the hypothesis that ptc encoded the Hh receptor [Ingham et al., *Nature*, 353:184–187 (1991)]. The activity of the ptc product, which is a multiple membrane spanning cell surface protein referred to as Patched [Hooper and Scott, supra], represses the wg and ptc genes and is antagonized by the Hh signal. Patched was proposed by Ingham et al. to be a constitutively active receptor which is inactivated by binding of Hh, thereby permitting transcription of Hh-responsive genes. As reported by Bejsovec and Wieschaus, *Development*, 119:501–517 (1993), however, Hh has effects in ptc null Drosophila embryos and thus cannot be the only Hh receptor. Accordingly, the role of Patched in Hh signalling has not been fully understood.

Goodrich et al. have isolated a murine patched gene [Goodrich et al., *Genes Dev.*, 10:301–312 (1996)]. Human patched homologues have also been described in recently published literature. For instance, Hahn et al., *Cell*, 85:841–851 (1996) describe isolation of a human homolog of Drosophila ptc. The gene displays up to 67% sequence identity at the nucleotide level and 60% similarity at the amino acid level with the Drosophila gene [Hahn et al., supra]. Johnson et al. also provide a predicted amino acid sequence of a human Patched protein [Johnson et al., *Science*, 272:1668–1671 (1996)]. Johnson et al. disclose that the 1447 amino acid protein has 96% and 40% identity to mouse and Drosophila Patched, respectively. The human and mouse data from these investigators suggest that patched is a single copy gene in mammals. According to Hahn et al., *Cell*, 85:841–851 (1996), analyses revealed the presence of three different 5' ends for their human ptc gene. Hahn et al. postulate there may be at least three different forms of the Patched protein in mammalian cells: the ancestral form represented by the murine sequence, and the two human forms. Patched is further discussed in a recent review by Marigo et al., *Development*, 122:1225 (1996).

Studies in Drosophila have also led to the hypothesis that Smo could be a candidate receptor for Hh [Alcedo et al., supra; van den Heuvel and Ingham, supra]. The smoothened (smo) gene was identified as a segment polarity gene and initially named smooth [Nusslein-Volhard et al., supra]. Since that name already described another locus, though, the segment polarity gene was renamed smoothened [Lindsley and Zimm, "The Genome of Drosophila melanogaster," San Diego, Calif.:Academic Press (1992)]. As first reported by Nusslein-Volhard et al., supra, the smo gene is required for the maintenance of segmentation in Drosophila embryos.

Alcedo et al., supra, have recently described the cloning of the Drosophila smoothened gene [see also, van den Heuvel and Ingham, supra]. Alcedo et al. report that hydropathy analysis predicts that the putative Smo protein is an integral membrane protein with seven membrane spanning alpha helices, a hydrophobic segment near the N-terminus, and a hydrophilic C-terminal tail. Thus, Smo may belong to the serpentine receptor family, whose members are all coupled to G proteins. Alcedo et al., supra, also report that smo is necessary for Hh signalling and that it acts downstream of hh and ptc.

As discussed in Pennisi, *Science*, 272:1583–1584 (1996), certain development genes are believed to play some role in cancer because they control cell growth and specialization. Recent studies suggest that patched is a tumor suppressor, or a gene whose loss or inactivation contributes to the excessive growth of cancer cells. Specifically, Hahn et al. and other investigators have found that patched is mutated in some common forms of basal cell carcinomas in humans [Hahn et al., *Cell*, 85:841–851 (1996); Johnson et al., supra; Gailani et al., in Letters, *Nature Genetics*, 13:September, 1996]. Hahn et al. report that alterations predicted to inactivate the patched gene product were found in six unrelated patients having basal cell nevus syndrome ("BCNS"), a familial complex of cancers and developmental abnormalities. Hahn et al. also report that the ptc pathway has been implicated in tumorigenesis by the cloning of the pancreatic tumor suppressor gene, DPC4. Vertebrate homologues of two other Drosophila segment polarity genes, the murine mammary Wntl [Rijsewijk et al., *Cell*, 50:649 (1987)] and the human glioblastoma GLI [Kinzler et al., *Science*, 236:70 (1987)], have also been implicated in cancer.

SUMMARY OF THE INVENTION

Applicants have identified cDNA clones that encode novel vertebrate Smoothened proteins, designated herein as "vSmo." In particular, cDNA clones encoding rat Smoothened and human Smoothened have been identified. The vSmo proteins of the invention have surprisingly been found to be co-expressed with Patched proteins and to form physical complexes with Patched. Applicants also discovered that the vSmo alone did not bind Sonic hedgehog but that vertebrate Patched homologues did bind Sonic hedgehog with relatively high affinity. It is believed that Sonic hedgehog may mediate its biological activities through a multi-subunit receptor in which vSmo is a signalling component and Patched is a ligand binding component, as well as a ligand regulated suppressor of vSmo. Accordingly, without being limited to any one theory, pathological conditions, such as basal cell carcinoma, associated with inactivated (or mutated) Patched may be the result of constitutive activity of vSmo or vSmo signalling following from negative regulation by Patched.

In one embodiment, the invention provides isolated vertebrate Smoothened. In particular, the invention provides isolated native sequence vertebrate Smoothened, which in one embodiment, includes an amino acid sequence comprising residues 1 to 793 of FIG. 1 (SEQ ID NO:2). The invention also provides isolated native sequence vertebrate Smoothened which includes an amino acid sequence comprising residues 1 to 787 of FIG. 4 (SEQ ID NO:4). In other embodiments, the isolated vertebrate Smoothened comprises at least about 80% identity with native sequence vertebrate Smoothened comprising residues 1 to 787 of FIG. 4 (SEQ ID NO:4).

In another embodiment, the invention provides chimeric molecules comprising vertebrate Smoothened fused to a heterologous polypeptide or amino acid sequence. An example of such a chimeric molecule comprises a vertebrate Smoothened fused to an epitope tag sequence.

In another embodiment, the invention provides an isolated nucleic acid molecule encoding vertebrate Smoothened. In one aspect, the nucleic acid molecule is RNA or DNA that encodes a vertebrate Smoothened, or is complementary to such encoding nucleic acid sequence, and remains stably bound to it under stringent conditions. In one embodiment, the nucleic acid sequence is selected from:

(a) the coding region of the nucleic acid sequence of FIG. 1 (SEQ ID NO:1) that codes for residue 1 to residue 793 (i.e., nucleotides 450–452 through 2826–2828), inclusive;

(b) the coding region of the nucleic acid sequence of FIG. 4 (SEQ ID NO:3) that codes for residue 1 to residue 787 (i.e., nucleotides 13–15 through 2371–2373), inclusive; or (c) a sequence corresponding to the sequence of (a) or (b) within the scope of degeneracy of the genetic code.

In a further embodiment, the invention provides a vector comprising the nucleic acid molecule encoding the vertebrate Smoothened. A host cell comprising the vector or the nucleic acid molecule is also provided. A method of producing vertebrate Smoothened is further provided.

In another embodiment, the invention provides an antibody which specifically binds to vertebrate Smoothened. The antibody may be an agonistic, antagonistic or neutralizing antibody.

In another embodiment, the invention provides non-human, transgenic or knock-out animals.

Another embodiment of the invention provides articles of manufacture and kits that include vertebrate Smoothened or vertebrate Smoothened antibodies.

A further embodiment of the invention provides protein complexes comprising vertebrate Smoothened protein and vertebrate Patched protein. In one embodiment the complexes further include vertebrate Hedgehog protein. The invention also provides vertebrate Patched which binds to vertebrate Smoothened. Optionally, the vertebrate Patched comprises a sequence which is a derivative of or fragment of a native sequence vertebrate Patched.

BRIEF DESCRIPTION OF THE DRAWINGS

The file of this patent contains at least three sheets of drawings executed in color. Copies this patent with color drawings wil be provided by the Patent and Trademark Office upon request and payment of the necessary fee.

FIGS. 1A–1F show the nucleotide (SEQ ID NO:1) and deduced amino acid sequence (SEQ ID NO:2) of native sequence rat Smoothened.

FIGS. 2A–2B show the primary structure of rat Smo (rSmo), (SEQ ID NO:2) and Drosophila Smo (dsmo) (SEQ ID NO:5). The signal peptide sequences are underlined, conserved amino acids are boxed, cysteines are marked with asterisks, potential glycosylation sites are marked with dashed boxes, and the seven hydrophobic transmembrane domains are shaded.

FIGS. 3A–3O show tissue distribution of SHH, Smo and Patched in embryonic and adult rat tissues. In situ hybridization of SHH (left column); Smo (middle column) and Patched (right column, not including insets) to rat tissues. Row E15 Sag, sagittal sections through E15 rat embryos. Rows E9, E10, E12, and E15, coronal sections through E9 neural folds, E10 neural tube and somites, E12 and E15 neural tube. Insets in Row E12 show sections through forelimb bud of E12 rat embryos. Legend- ht=heart; sk=skin; bl=bladder; ts=testes; lu=lung; to=tongue; vtc=vertebral column; nf=neural fold; nc=notocord; so=somite; fp=floor plate; vh=ventral horn; vz=ventricular zone; cm=cardiac mesoderm and vm=ventral midbrain.

FIGS. 4A–4E show the nucleotide (SEQ ID NO:3) and deduced amino acid sequence (SEQ ID NO:4) for native sequence human Smoothened.

FIGS. 5A–5E show the primary structure of human Smo (hsmo) (SEQ ID NO:4) and rat Smo (rat.Smo) (SEQ ID NO:2), and homology to Drosophila Smo (dros.smo) (SEQ ID NO:5). Conserved amino acids are boxed.

FIGS. 6A–6I illustrate the results of binding and co-immunoprecipitation assays which show SHH-N binds to mPatched but not to rSmo. Staining of cells expressing the Flag tagged rSmo (a and b) or Myc tagged mPatched (c, d, and e) with (a) Flag (Smo) antibody; (c) Myc (mPatched) antibody; (b and d) IgG-SHH-N; or (e) Flag tagged SHH-N. (f) Co-immunoprecipitation of epitope tagged mPatched (Patched) or epitope tagged rSmo (Smo) with IgG-SHH-N. (g) cross-linking of $^{125}$I-SHH-N ($^{125}$I-SHH) to cells expressing mPatched or rSmo in the absence or presence of unlabeled SHH-N. (h) Co-immunoprecipitation of $^{125}$I-SHH by an epitope tagged mPatched (Patched) or an epitope tagged rSmo (Smo). (i) competition binding of $^{125}$I-SHH to cells expressing mPatched or mPatched plus rSmo.

FIGS. 7A–7E illustrate (a) Double immunohistochemical staining of Patched (red) and Smo (green) in transfected cells. Yellow indicates co-expression of the two proteins; (b and c) Detection of Patched-Smo Complex by immunoprecipitation; (b) Immunoprecipitation with antibodies to the epitope tagged Patched and analysis on a Western blot with antibodies to epitope tagged Smo; (c) immunoprecipitation with antibodies to the epitope tagged Smo and analysis on a Western blot with antibodies to epitope tagged Patched. (d and e) Co-immunoprecipitation of $^{125}$I-SHH bound to cells expressing both Smo and Patched with antibodies to either Smo (d) or Patched (e) epitope tags.

FIG. 8 shows a Western blot from a SDS-gel depicting the expression level of a wildtype (WT) and mutated Patched (mutant).

FIG. 9 shows a model describing the putative SHH receptor and its proposed activation by SHH. As shown in the model, Patched is a ligand binding component and vSmo is a signalling component in a multi-subunit SHH receptor.

DETAILED DESCRIPTION OF THE PREFERRED EMBODIMENTS

I. Definitions

The terms "vertebrate Smoothened", "vertebrate Smoothened protein" and "vSmo" when used herein encompass native sequence vertebrate Smoothened and vertebrate Smoothened variants (each of which is defined herein). These terms encompass Smoothened from a variety of animals classified as vertebrates, including mammals. In a preferred embodiment, the vertebrate Smoothened is rat Smoothened (rSmo) or human Smoothened (hSmo). The vertebrate Smoothened may be isolated from a variety of sources, such as from human tissue types or from another source, or prepared by recombinant or synthetic methods.

A "native sequence vertebrate Smoothened" comprises a protein having the same amino acid sequence as a vertebrate Smoothened derived from nature. Thus, a native sequence vertebrate Smoothened can have the amino acid sequence of naturally occurring human Smoothened, rat Smoothened, or Smoothened from any other vertebrate. Such native sequence vertebrate Smoothened can be isolated from nature or can be produced by recombinant or synthetic means. The term "native sequence vertebrate Smoothened" specifically encompasses naturally-occurring truncated forms of the vertebrate Smoothened, naturally-occurring variant forms (e.g., alternatively spliced forms) and naturally-occurring allelic variants of the vertebrate Smoothened. In one embodiment of the invention, the native sequence vertebrate Smoothened is a mature native sequence Smoothened comprising the amino acid sequence of SEQ ID NO:4. In another embodiment of the invention, the native sequence vertebrate Smoothened is a mature native sequence Smoothened comprising the amino acid sequence of SEQ ID NO:2.

"Vertebrate Smoothened variant" means a vertebrate Smoothened as defined below having less than 100% sequence identity with vertebrate Smoothened having the deduced amino acid sequence shown in SEQ ID NO:4 for human Smoothened or SEQ ID NO:2 for rat Smoothened. Such vertebrate Smoothened variants include, for instance, vertebrate Smoothened proteins wherein one or more amino acid residues are added at the N- or C-terminus of, or within, the sequences of SEQ ID NO:4 or SEQ ID NO:2; wherein about one to thirty amino acid residues are deleted, or optionally substituted by one or more amino acid residues; and derivatives thereof, wherein an amino acid residue has been covalently modified so that the resulting product has a non-naturally occurring amino acid. Ordinarily, a vertebrate Smoothened variant will have at least about 80% sequence identity, more preferably at least about 90% sequence identity, and even more preferably at least about 95% sequence identity with the sequence of SEQ ID NO:4 or SEQ ID NO:2.

The term "epitope tag" when used herein refers to a tag polypeptide having enough residues to provide an epitope against which an antibody thereagainst can be made, yet is short enough such that it does not interfere with activity of the vertebrate Smoothened. The tag polypeptide preferably also is fairly unique so that the antibody thereagainst does not substantially cross-react with other epitopes. Suitable tag polypeptides generally have at least six amino acid residues and usually between about 8–50 amino acid residues (preferably between about 9–30 residues).

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous substances. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the vSmo natural environment will not be present. Ordinarily, however, isolated protein will be prepared by at least one purification step.

An "isolated" vSmo nucleic acid molecule is a nucleic acid molecule that is identified and separated from at least one contaminant nucleic acid molecule with which it is ordinarily associated in the natural source of the vSmo nucleic acid. An isolated vSmo nucleic acid molecule is other than in the form or setting in which it is found in nature. Isolated vSmo nucleic acid molecules therefore are distinguished from the vSmo nucleic acid molecule as it exists in natural cells. However, an isolated vSmo nucleic acid molecule includes vSmo nucleic acid molecules contained in cells that ordinarily express vSmo where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-vSmo monoclonal antibodies (including agonist, antagonist, and neutralizing antibodies) and anti-vSmo antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-vSmo antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired activity. See, e.g. U.S. Pat. No. 4,816,567 and Mage et al., in *Monoclonal Antibody Production Techniques and Applications*, pp.79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552–554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

The term "vertebrate" as used herein refers to any animal classified as a vertebrate including certain classes of fish, reptiles, birds, and mammals. The term "mammal" as used herein refers to any animal classified as a mammal, including humans, cows, rats, mice, horses, dogs and cats.

II. Modes For Carrying Out The Invention

The present invention is based on the discovery of vertebrate homologues of Smoothened. In particular, Applicants have identified and isolated human and rat Smoothened. The properties and characteristics of human and rat Smoothened are described in further detail in the Examples below. Based upon the properties and characteristics of human and rat Smoothened disclosed herein, it is Applicants' present belief that vertebrate Smoothened is a signalling component in a multi-subunit Hedgehog (particularly Sonic Hedgehog "SHH") receptor.

A description follows as to how vertebrate Smoothened may be prepared.

A. Preparation of vSmo

Techniques suitable for the production of vSmo are well known in the art and include isolating vSmo from an endogenous source of the polypeptide, peptide synthesis (using a peptide synthesizer) and recombinant techniques (or any combination of these techniques). The description below relates primarily to production of vSmo by culturing cells transformed or transfected with a vector containing vSmo nucleic acid. It is of course, contemplated that alternative methods, which are well known in the art, may be employed to prepare vSmo.

1. Isolation of DNA Encoding vSmo

The DNA encoding vSmo may be obtained from any cDNA library prepared from tissue believed to possess the vSmo mRNA and to express it at a detectable level. Accordingly, human Smo DNA can be conveniently obtained from a cDNA library prepared from human tissues, such as the library of human embryonic lung cDNA described in Example 3. Rat Smo DNA can be conveniently obtained from a cDNA library prepared from rat tissues, such as described in Example 1. The vSmo-encoding gene may also be obtained from a genomic library or by oligonucleotide synthesis.

Libraries can be screened with probes (such as antibodies to the vSmo or oligonucleotides or polypeptides as described in the Examples) designed to identify the gene of interest or the protein encoded by it. The probes are preferably labeled such that they can be detected upon hybridization to DNA in the library being screened. Methods of labeling are well known in the art, and include the use of radiolabels like $^{32}$P-labeled ATP, biotinylation or enzyme labeling. Screening the cDNA or genomic library with a selected probe may be conducted using standard procedures, such as described in Sambrook et al., *Molecular Cloning: A Laboratory Manual* (New York: Cold Spring Harbor Laboratory Press, 1989). An alternative means to isolate the gene encoding vSmo is to use PCR methodology [Sambrook et al., supra; Dieffenbach et al., *PCR Primer:A Laboratory Manual* (Cold Spring Harbor Laboratory Press, 1995)].

Nucleic acid having all the protein coding sequence may be obtained by screening selected cDNA or genomic libraries using the deduced amino acid sequences disclosed herein, and, if necessary, using conventional primer extension procedures as described in Sambrook et al., supra, to detect precursors and processing intermediates of mRNA that may not have been reverse-transcribed into cDNA.

vSmo variants can be prepared by introducing appropriate nucleotide changes into the vSmo DNA, or by synthesis of the desired vSmo polypeptide. Those skilled in the art will appreciate that amino acid changes (compared to native sequence vSmo) may alter post-translational processes of the vSmo, such as changing the number or position of glycosylation sites.

Variations in the native sequence vSmo can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

2. Insertion of Nucleic Acid into A Replicable Vector

The nucleic acid (e.g., cDNA or genomic DNA) encoding vSmo may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below.

(i) Signal Sequence Component

The vSmo may be produced recombinantly not only directly, but also as a fusion polypeptide with a heterologous amino acid sequence or polypeptide, which may be a signal sequence or other polypeptide having a specific cleavage site at the N-terminus of the mature protein or polypeptide. In general, the signal sequence may be a component of the vector, or it may be a part of the vSmo DNA that is inserted into the vector. The heterologous signal sequence selected preferably is one that is recognized and processed (i.e., cleaved by a signal peptidase) by the host cell.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses.

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of vSmo DNA.

(iii) Selection Gene Component

Expression and cloning vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin [Southern et al., *J. Molec. Appl. Genet.*, 1:327 (1982)], mycophenolic acid (Mulligan et al., *Science*, 209:1422 (1980)] or hygromycin [Sugden et al., *Mol. Cell. Biol.*, 5:410–413 (1985)]. The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the vSmo nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes vSmo. Amplification is the process by which genes in greater demand for the production of a protein critical for growth are reiterated in tandem within the chromosomes of successive generations of recombinant cells.

Cells transformed with the DHFR selection gene may first be identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding vSmo.

(iv) Promoter Component

Expression and cloning vectors usually contain a promoter that is recognized by the host organism and is operably linked to the vSmo nucleic acid sequence. Promoters are untranslated sequences located upstream (5') to the start codon of a structural gene (generally within about 100 to 1000 bp) that control the transcription and translation of particular nucleic acid sequence, such as the vSmo nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to vSmo encoding DNA by removing the promoter from the source DNA by restriction enzyme digestion and inserting the isolated promoter sequence into the vector.

Promoters suitable for use with prokaryotic hosts include the -lactamase and lactose promoter systems [Chang et al., *Nature*, 275:617–624 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)].

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., *J. Biol. Chem.*, 255:12073–12080 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in EP 73,657.

vSmo transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter.

The early and late promoters of the SV40 virus are conveniently obtained as an SV40 restriction fragment that also contains the SV40 viral origin of replication [Fiers et al., *Nature*, 273:113 (1978); Mulligan and Berg, *Science*, 209:1422–1427 (1980); Pavlakis et al., *Proc. Natl. Acad. Sci. USA*, 78:7398–7402 (1981)]. The immediate early promoter of the human cytomegalovirus is conveniently obtained as a HindIII E restriction fragment [Greenaway et al., *Gene*, 18:355–360 (1982)]. A system for expressing DNA in mammalian hosts using the bovine papilloma virus as a vector is disclosed in U.S. Pat. No. 4,419,446. A modification of this system is described in U.S. Pat. No. 4,601,978 [See also Gray et al., *Nature*, 295:503–508 (1982) on expressing cDNA encoding immune interferon in monkey cells; Reyes et al., *Nature*, 297:598–601 (1982) on expression of human-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon 1 gene in cultured mouse and rabbit cells; and Gorman et al., *Proc. Natl. Acad. Sci. USA*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter].

(v) Enhancer Element Component

Transcription of a DNA encoding the vSmo by higher eukaryotes may be increased by inserting an enhancer sequence into the vector. Enhancers are cis-acting elements of DNA, usually about from 10 to 300 bp, that act on a promoter to increase its transcription. Enhancers are relatively orientation and position independent, having been found 5' [Laimins et al., *Proc. Natl. Acad. Sci. USA*, 78:464–468 (1981]) and 3' [Lusky et al., *Mol. Cell Bio.*, 3:1108 (1983]) to the transcription unit, within an intron [Banerji et al., *Cell*, 33:729 (1983)], as well as within the coding sequence itself [Osborne et al., *Mol. Cell Bio.*, 4:1293 (1984)]. Many enhancer sequences are now known from mammalian genes (globin, elastase, albumin, -fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters.

(vi) Transcription Termination Component

Expression vectors used in eukaryotic host cells (yeast, fungi, insect, plant, animal, human, or nucleated cells from other multicellular organisms) will also typically contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding vSmo.

(vii) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxam et al., *Methods in Enzymology*, 65:499 (1980).

(viii) Transient Expression Vectors

Expression vectors that provide for the transient expression in mammalian cells of DNA encoding vSmo may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired aproperties.

(ix) Suitable Exemplary Vertebrate Cell Vectors

Other methods, vectors, and host cells suitable for adaptation to the synthesis of vSmo in recombinant vertebrate cell culture are described in Gething et al., *Nature*, 293:620–625 (1981); Mantei et al., *Nature*, 281:40–46 (1979); EP 117,060; and EP 117,058.

3. Selection and Transformation of Host Cells

Suitable host cells for cloning or expressing the DNA in the vectors herein are the prokaryote, yeast, or higher eukaryote cells described above. Suitable prokaryotes for this purpose include but are not limited to eubacteria, such as Gram-negative or Gram-positive organisms, for example, Enterobacteriaceae such as Escherichia. Preferably, the host cell should secrete minimal amounts of proteolytic enzymes.

In addition to prokaryotes, eukaryotic microbes such as filamentous fungi or yeast may be suitable cloning or expression hosts for vSmo-encoding vectors. Saccharomyces cerevisiae, or common baker's yeast, is the most commonly used among lower eukaryotic host microorganisms. However, a number of other genera, species, and strains are commonly available and useful herein.

Suitable host cells for the expression of glycosylated vSmo are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells.

Propagation of vertebrate cells in culture (tissue culture) is also well known in the art [See, e.g., *Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44–68 (1982)); MRC 5 cells; and FS4 cells.

Host cells are transfected and preferably transformed with the above-described expression or cloning vectors for vSmo production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., *Gene*, 23:315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham and van der Eb, *Virology*, 52:456–457 (1973) is preferred. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

4. Culturing the Host Cells

Prokaryotic cells used to produce vSmo may be cultured in suitable media as described generally in Sambrook et al., supra.

The mammalian host cells used to produce vSmo may be cultured in a variety of media. Examples of commercially available media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Various labels may be employed, most commonly radioisotopes, and particularly $_{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, or luminescent labels.

Antibodies useful for immunohistochemical staining and/or assay of sample fluids may be either monoclonal or polyclonal, and may be prepared in any mammal. Conveniently, the antibodies may be prepared against a native sequence vSmo protein or against a synthetic peptide based on the DNA sequences provided herein.

6. Purification of vSmo

It is contemplated that it may be desired to purify some form of vSmo from recombinant cell proteins or polypeptides to obtain preparations that are substantially homogeneous as to vSmo. As a first step, the culture medium or lysate may be centrifuged to remove particulate cell debris. vSmo thereafter may be purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. vSmo variants may be recovered in the same fashion as native sequence vSmo, taking account of any substantial changes in properties occasioned by the variation.

A protease inhibitor such as phenyl methyl sulfonyl fluoride (PMSF) also may be useful to inhibit proteolytic degradation during purification, and antibiotics may be included to prevent the growth of adventitious contaminants.

7. Covalent Modifications of vSmo

Covalent modifications of vSmo are included within the scope of this invention. One type of covalent modification of the vSmo included within the scope of this invention comprises altering the native glycosylation pattern of the protein. "Altering the native glycosylation pattern" is intended for purposes herein to mean deleting one or more carbohydrate moieties found in native sequence vSmo, and/or adding one or more glycosylation sites that are not present in the native sequence vSmo.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the vSmo may be accomplished by altering the amino acid sequence such that it contains one or more of the above-described tripeptide sequences (for N-linked glycosylation sites). The alteration may also be made by the addition of, or substitution by, one or more serine or threonine residues to the native sequence vSmo (for O-linked glycosylation sites). The vSmo amino acid sequence may optionally be altered through changes at the DNA level, particularly by mutating the DNA encoding the vSmo protein at preselected bases such that codons are generated that will translate into the desired amino acids. The DNA mutation(s) may be made using methods described above and in U.S. Pat. No. 5,364,934, supra.

Another means of increasing the number of carbohydrate moieties on the vSmo is by chemical or enzymatic coupling of glycosides to the polypeptide. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, *CRC Crit. Rev. Biochem.*, pp. 259–306 (1981).

Removal of carbohydrate moieties present on the vSmo protein may be accomplished chemically or enzymatically or by mutational substitution of codons encoding for amino acid residues that serve as targets for glycosylation. For instance, chemical deglycosylation by exposing the polypeptide to the compound trifluoromethanesulfonic acid, or an equivalent compound can result in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Glycosylation at potential glycosylation sites may be prevented by the use of the compound tunicamycin as described by Duksin et al., J. Biol. Chem., 257:3105 (1982). Tunicamycin blocks the formation of protein-N-glycoside linkages.

8. vSmo Chimeras

The present invention also provides chimeric molecules comprising vSmo fused to another, heterologous amino acid sequence or polypeptide. In one embodiment, the chimeric molecule comprises a fusion of the vSmo with a tag polypeptide which provides an epitope to which an anti-tag antibody can selectively bind. The epitope tag is generally provided at the amino- or carboxyl-terminus of the vSmo. Such epitope-tagged forms of the vSmo are desirable as the presence thereof can be detected using a labeled antibody against the tag polypeptide. Also, provision of the epitope tag enables the vSmo to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 [Field et al., *Mol. Cell. Biol*., 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Enaineering*, 3(6) :547–553 (1990)]. Other tag polypeptides have been disclosed. Examples include the Flag-peptide [Hopp et al., *BioTechnology*, 6:1204–1210 (1988)]; the KT3 epitope peptide [Martin et al., *Science*, 255:192–194 (1992)]; an -tubulin epitope peptide [Skinner et al., *J. Biol. Chem*., 266:14163–14166 (1991)]; and the T7 gene 10 protein peptide tag [Lutz-Freyermuth et al., *Proc. Natl. Acad. Sci. USA*, 87:6393–6397 (1990)]. Once the tag polypeptide has been selected, an antibody thereto can be generated using the techniques disclosed herein.

The general methods suitable for the construction and production of epitope-tagged vSmo are the same as those disclosed hereinabove. vSmo-tag polypeptide fusions are most conveniently constructed by fusing the cDNA sequence encoding the vSmo portion in-frame to the tag polypeptide DNA sequence and expressing the resultant DNA fusion construct in appropriate host cells. Ordinarily, when preparing the vSmo-tag polypeptide chimeras of the present invention, nucleic acid encoding the vSmo will be fused at its 3' end to nucleic acid encoding the N-terminus of the tag polypeptide, however 5' fusions are also possible.

9. Methods of Using vSmo vSmo, as disclosed in the present specification, has utility in therapeutic and non-therapeutic applications. As a therapeutic, vSmo (or the nucleic acid encoding the same) can be employed in in vivo or ex vivo gene therapy techniques. In non-therapeutic applications, nucleic acid sequences encoding the vSmo may be used as a diagnostic for tissue-specific typing. For example, procedures like in situ hybridization, Northern and Southern blotting, and PCR analysis may be used to determine whether DNA and/or RNA encoding vSmo is present in the cell type(s) being evaluated. vSmo nucleic acid will also be useful for the preparation of vSmo by the recombinant techniques described herein.

The isolated vSmo may be used in quantitative diagnostic assays as a control against which samples containing unknown quantities of vSmo may be prepared. vSmo preparations are also useful in generating antibodies, as standards in assays for vSmo (e.g., by labeling vSmo for use as a standard in a radioimmunoassay, radioreceptor assay, or enzyme-linked immunoassay), and in affinity purification techniques.

Nucleic acids which encode vSmo, such as the rat vSmo disclosed herein, can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, rat cDNA encoding rSmo or an appropriate sequence thereof can be used to clone genomic DNA encoding Smo in accordance with established techniques and the genomic sequences used to generate transgenic animals that contain cells which express DNA encoding Smo. Methods for generating transgenic animals, particularly animals such as mice or rats, have become conventional in the art and are described, for example, in U.S. Pat. Nos. 4,736,866 and 4,870,009. Typically, particular cells would be targeted for vSmo transgene incorporation with tissue-specific enhancers. Transgenic animals that include a copy of a transgene encoding vSmo introduced into the germ line of the animal at an embryonic stage can be used to examine the effect of increased expression of DNA encoding vSmo. Such animals can be used as tester animals for reagents thought to confer protection from, for example, pathological conditions associated with constitutive activity of vSmo or Hedgehog, including some forms of cancer that may result therefrom, such as for example, basal cell carcinoma, basal cell nevus syndrome and pancreatic carcinoma. In accordance with this facet of the invention, an animal is treated with the reagent and a reduced incidence of the pathological condition, compared to untreated animals bearing the transgene, would indicate a potential therapeutic intervention for the pathological condition.

Alternatively, the non-human homologues of vSmo can be used to construct a vsmo "knock out" animal which has a defective or altered gene encoding vSmo as a result of homologous recombination between the endogenous gene encoding vSmo and altered genomic DNA encoding vSmo introduced into an embryonic cell of the animal. For example, rat cDNA encoding Smo can be used to clone genomic DNA encoding Smo in accordance with established techniques. A portion of the genomic DNA encoding Smo can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–151]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and can be used in the study of the mechanism by which the Hedgehog family of molecules exerts mitogenic, differentiative, and morphogenic effects.

B. Anti-vSmo Antibody Preparation

The present invention further provides anti-vSmo antibodies. Antibodies against vSmo may be prepared as follows. Exemplary antibodies include polyclonal, monoclonal, humanized, bispecific, and heteroconjugate antibodies.

1. Polyclonal Antibodies

The vSmo antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the vSmo protein or a fusion protein thereof. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for antibody titer. If desired, the mammal can be boosted until the antibody titer increases or plateaus.

2. Monoclonal Antibodies

The vSmo antibodies may, alternatively, be monoclonal antibodies. Monoclonal antibodies may be prepared using hybridoma methods, such as those described by Kohler and Milstein, supra. In a hybridoma method, a mouse, hamster, or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

The immunizing agent will typically include the vsmo protein or a fusion protein thereof. Cells expressing vSmo at their surface may also be employed. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against vSmo. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an $F(ab')_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

3. Humanized Antibodies

The vSmo antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–327 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al., J. Immunol., 151:2296 (1993); Chothia and Lesk, J. Mol. Biol., 196:901 (1987)]. Another method uses a particular framework derived from the consensus sequence of all human antibodies of a particular subgroup of light or heavy chains. The same framework may be used for several different humanized antibodies [Carter et al., Proc. Natl. Acad. Sci. USA, 89:4285 (1992); Presta et al., J. Immunol., 151:2623 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published Mar. 3, 1994].

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region ($J_H$) gene in chimeric and germline mutant mice results in complete inhibition of endogenous antibody production. Transfer of the human germ-line immunoglobulin gene array in such germ-line mutant mice will result in the production of human antibodies upon antigen challenge [see, e.g., Jakobovits et al., *Proc. Natl. Acad. Sci. USA*, 90:2551–255 (1993); Jakobovits et al., *Nature*, 362:255–258 (1993); Bruggemann et al., *Year in Immuno.*, 7:33 (1993)]. Human antibodies can also be produced in phage display libraries [Hoogenboom and Winter, *J. Mol. Biol.*, 227:381 (1991); Marks et al., *J. Mol. Biol.*, 222:581 (1991)]. The techniques of Cote et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)].

4. Bispecific Antibodies

Bispecific antibodies are monoclonal, preferably human or humanized, antibodies that have binding specificities for at least two different antigens. In the present case, one of the binding specificities is for the vSmo, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Millstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J*., 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy-chain/light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/20373; EP 003089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Uses of vSmo Antibodies vSmo antibodies may be used in diagnostic assays for vSmo, e.g., detecting its expression in specific cells or tissues. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth*., 40:219 (1981); and Nygren, *J. Histochem. and Cytochem*., 30:407 (1982).

vSmo antibodies also are useful for the affinity detection or purification of vSmo from recombinant cell culture or natural sources. In this process, the antibodies against vSmo are immobilized on a suitable support, such a Sephadex resin or filter paper, using methods well known in the art. The immobilized antibody then is contacted with a sample containing the vSmo, and thereafter the support is washed with a suitable solvent that will remove substantially all the material in the sample except the vSmo, which is bound to the immobilized antibody. Finally, the support is washed with another suitable solvent that will release the vSmo from the antibody.

The vSmo antibodies may also be employed as therapeutics. For example, vSmo antibodies may be used to block or neutralize excess vSmo signalling that may result from mutant or inactivated Patched. Accordingly, the vSmo antibodies may be used in the treatment of, or amelioration of symptoms caused by, a pathological condition resulting from or associated with excess vSmo or vSmo signalling. Optionally, agonistic vSmo antibodies can be employed to induce the formation of, or enhance or stimulate tissue regeneration, such as regeneration of skin tissue, lung tissue, muscle (such as heart or skeletal muscle), neural tissue (such as serotonergic neurons, motoneurons or straital neurons), bone tissue or gut tissue. This vSmo antibody therapy will be useful in instances where the tissue has been damaged by disease, aging or trauma.

The vSmo antibodies may be used or administered to a patient in a pharmaceutically-acceptable carrier. Suitable carriers and their formulations are described in *Remington's Pharmaceutical Sciences*, 16th ed., 1980, Mack Publishing Co., edited by Oslo et al. If the vSmo antibodies are to be administered to a patient, the antibodies can be administered by injection (e.g., intravenous, intraperitoneal, subcutaneous, intramuscular), or by other methods such as infusion that ensure its delivery to the bloodstream in an effective form. Effective dosages and schedules for administering the vSmo antibodies may be determined empirically, and making such determinations is within the skill in the art. Those skilled in the art will understand that the dosage of vSmo antibodies that must be administered will vary depending on, for example, the patient which will receive the antibodies, the route of administration, and other therapeutic agents being administered to the mammal. Guidance in selecting appropriate doses for such vSmo antibodies is found in the literature on therapeutic uses of antibodies, e.g., *Handbook of Monoclonal Antibodies*, Ferrone et al., eds., Noges Publications, Park Ridge, N.J., (1985) ch. 22 and pp. 303–357; Smith et al., *Antibodies in Human Diagnosis and Therapy*, Haber et al., eds., Raven Press, New York (1977) pp. 365–389. A typical daily dosage of the vSmo antibodies used alone might range from about 1 g/kg to up to 100 mg/kg of body weight or more per day, depending on the factors mentioned above.

C. Kits Containing vSmo or vSmo Antibodies

In another embodiment of the invention, there are provided articles of manufacture and kits containing vSmo or vSmo antibodies. The article of manufacture typically comprises a container with a label. Suitable containers include, for example, bottles, vials, and test tubes. The containers may be formed from a variety of materials such as glass or plastic. The container holds the vSmo or vSmo antibodies. The label on the container may indicate directions for either in vivo or in vitro use, such as those described above.

The kit of the invention will typically comprise the container described above and one or more other containers comprising materials desirable from a commercial and user standpoint, including buffers, diluents, filters, and package inserts with instructions for use.

D. Additional Compositions of Matter

In a further embodiment of the invention, there are provided protein complexes comprising vertebrate Smoothened protein and vertebrate Patched protein. As demonstrated in the Examples, vertebrate Smoothened and vertebrate Patched can form a complex. The protein complex which includes vertebrate Smoothened and vertebrate Patched may also include vertebrate Hedgehog protein. Typically in such a complex, the vertebrate Hedgehog binds to the vertebrate Patched but does not bind to the vertebrate Smoothened. In a preferred embodiment, the complex comprising vertebrate Smoothened and vertebrate Patched is a receptor for vertebrate Hedgehog.

The invention also provides a vertebrate Patched which binds to vertebrate Smoothened. Optionally the vertebrate Patched comprises a sequence which is a derivative of or fragment of a native sequence vertebrate Patched. The vertebrate Patched will typically consist of a sequence which has less than 100' sequence identity with a native sequence vertebrate Patched. In one embodiment, the vertebrate Patched directly and specifically binds vertebrate Smoothened. Alternatively, it is contemplated that the vertebrate Patched may bind vertebrate Smoothened indirectly.

The following examples are offered for illustrative purposes only, and are not intended to limit the scope of the present invention in any way.

All references cited in the present specification are hereby incorporated by reference in their entirety.

EXAMPLES

All commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard Manassas VA 20110-2209.

Example 1

Isolation and Cloning of Rat Smoothened cDNA

Full-length rat Smoothened cDNA was isolated by low stringency hybridization screening of 1.2×106 plaques of an embryonic day 9–10 rat cDNA library (containing cDNAs size-selected >1500 base pairs), using the entire coding region of Drosophila Smoothened [Alcedo et. al., supra] (labeled with $^{32}$P-dCTP) as a probe. The library was prepared by cloning cDNA inserts into the NotI site of a lambda RK18 vector [Klein et. al., *Proc. Natl. Acad. Sci.*, 93:7108–7113 (1996)] following XmnI adapters ligation. Conditions for hybridization were: 5×SSC, 30% formamide, 5×Denhardt's, 50 mM sodium phosphate (pH 6.5), 5% dextran sulfate, 0.1% SDS and 50 μg/ml salmon sperm DNA, overnight at 42° C. Nitrocellulose filters were washed to a stringency of 1×SSC at 42° C., and exposed overnight to Kodak X-AR film. Three of eight positive plaques were selected for further purification. After amplification of the plaque-purified phage, phagemid excision products were generated by growing M13 helper phage (M13K07; obtained from New England Biolabs), bacteria (BB4; obtained from Stratagene), and the purified phage together in a 100:10:1 ratio. Plasmid DNA was recovered by Qiagen purification from ampicillin-resistant colonies following infection of BB4 with the excised purified phagemid.

Sequencing of the three cDNAs showed them to be identical, with the exception that two contained only a partial coding sequence, whereas the third contained the entire open reading frame of rat Smoothened, including 449 and 1022 nucleotides, respectively of 5' and 3' untranslated sequence and a poly-A tail. This cDNA clone was sequenced completely on both strands.

The entire nucleotide sequence of rat Smoothened (rSmo) is shown in FIG. 1 (SEQ ID NO:1) (reference is also made to Applicants' ATCC deposit of the rat Smoothened in pRK5. rsmo.AR140, assigned ATCC Dep. No. 98165). The cDNA contained an open reading frame with a translational initiation site assigned to the ATG codon at nucleotide positions 450–452. The open reading frame ends at the termination codon at nucleotide positions 2829–2831.

The predicted amino acid sequence of the rat Smoothened (rSmo) contains 793 amino acids (including a 32 amino acid signal peptide), as shown in FIG. 1 (SEQ ID NO:2). rSmo appears to be a typical seven transmembrane (7 TM), G protein-coupled receptor, containing 4 potential N-glycosylation sites and a 203 amino acid long putative extracellular amino-terminus domain which contains 13 stereotypically spaced cysteines (see FIG. 2).

An alignment of the rSmo sequence with sequences for dSmo, wingless receptor and vertebrate Frizzled revealed that rSmo is 33% homologous to the dSmo sequence reported in Alcedo et al., supra (50% homologous in the transmembrane domains); 23% homologous to the wingless receptor sequence reported in Bhanot et al., supra; and 25% homologous to the vertebrate Frizzled sequence reported in Chan et al., supra.

Example 2

In Situ Hybridization and Northern Blot Analysis

In situ hybridization and Northern blot analyses were conducted to examine tissue distribution of Smo, Patched and SHH in embryonic and adult rat tissues.

For in situ hybridization, E9-E15.5 rat embryos (Hollister Labs) were immersion-fixed overnight at 4° C. in 4% paraformaldehyde, then cryoprotected overnight in 20% sucrose. Adult rat brains and spinal cords were frozen fresh. All tissues were sectioned at 16 um, and processed for in situ hybridization using $^{33}$P-UTP labelled RNA probes as described in Treanor et al., Nature, 382:80–83 (1996). Sense and antisense probes were derived from the N-terminal region of rSmo using T7 polymerase. The probe used to detect SHH was antisense to bases 604–1314 of mouse SHH [Echelard et al., Cell, 75:1417–1430 (1993)]. The probe used to detect Patched was antisense to bases 502–1236 of mouse Patched [Goodrich et al., supra]. Reverse transcriptase polymerase chain reaction analysis was performed as described in Treanor et al., supra.

For Northern blot analysis, a rat multiple tissue Northern blot (Clontech) was hybridized and washed at high stringency according to the manufacturer's protocol, using a $^{32}$P-dCTP-labelled probe encompassing the entire rSmo coding region.

The results are illustrated in FIG. 3. By in situ hybridization and Northern blot analysis, expression of rSmo mRNA was detected from E9 onward in SHH responsive tissues such as the neural folds and early neural tube [Echelard et al., supra, Krauss et al., supra); Roelink et al., supra], pre-somitic mesoderm and somites (Johnson et al., supra; Fan et al., supra], and developing limb buds [Riddle et al., supra] gut (Roberts et al., supra] and eye [Krauss et al., supra]. Rat Smo transcripts were also found in tissues whose development is regulated by other members of the vertebrate HH protein family such as testes (desert HH) [Bitgood et al., Curr. Biol., 6:298–304 (1996)], cartilage (indian HH) [Vortkamp et al., Science, 273:613–622 (1996)], and muscle (the zebra fish, echinida HH) [Currie and Ingham, Nature, 382:452–455 (1996)] (See e.g., FIG. 3; other data not shown). In all of the above recited tissues, rSmo appeared to be co-expressed with rPatched.

rSmo and rPatched mRNAs were also found in and around SHH expressing cells in the embryonic lung, epiglottis, thymus, vertebral column, tongue, jaw, taste buds and teeth (FIG. 3). In the embryonic nervous system, rSmo and rPatched are initially expressed throughout the neural plate; by E12, however, their expression declines in lateral parts of the neural tube, and by P1, was restricted to cells in relatively close proximity to the ventricular zone (FIG. 3). In the adult rat tissues, rSmo expression was maintained in the brain, lung, kidney, testis, heart and spleen (data not shown).

Example 3

Isolation and Cloning of Human Smoothened cDNA

A cDNA probe corresponding to the coding region of the rat smoothened gene (described in Example 1 above) was labeled by the random hexanucleotide method and used to screen $10^6$ clones of a human embryonic lung cDNA library (Clontech, Inc.) in lgt10. Duplicate filters were hybridized at 42° C. in 50% formamide, 5×SSC, 10×Denhardt's, 0.05M sodium phosphate (pH 6.5), 0.1% sodium pyrophosphate, 50 μg/ml of sonicated salmon sperm DNA. Filters were rinsed in 2×SSC and then washed once in 0.5×SSC, 0.1% SDS at 42° C. Hybridizing phage were plaque-purified and the cDNA inserts were subcloned into pUC 118 (New England Biolabs). Two clones, 5 and 14, had overlapping inserts of approximately 2 and 2.8 kb respectively, covering the entire human Smoothened coding sequence (See FIG. 4). Clones 5 and 14 have been deposited by Applicants with ATCC as puc.118. hsmo.5 and puc.118. hsmo.14, respectively, and assigned ATCC Dep. Nos. 98162 and 98163, respectively. Both strands were sequenced by standard fluorescent methods on an ABI377 automated sequencer.

The entire nucleotide sequence of human Smoothened is shown in FIG. 4 (SEQ ID NO:3). The cDNA contained an open reading frame with a translational initiation site assigned to the ATG codon at nucleotide positions 13–15. The open reading frame ends at the termination codon at nucleotide positions 2374–2376.

The predicted amino acid sequence of the human Smoothened (hSmo) contains 787 amino acids (including a 29 amino acid signal peptide), as shown in FIG. 4 (SEQ ID NO:4). hSmo appears to be a typical seven transmembrane (7 TM), G protein-coupled receptor, containing 5 potential N-glycosylation sites and a 202 amino acid long putative extracellular amino-terminus domain which contains 13 stereotypically spaced cysteines.

An alignment of the predicted hSmo amino acid sequence and rSmo sequence (see Example 1) revealed 94% amino acid identity.

An alignment of the hSmo sequence with sequences for dsmo, wingless receptor and vertebrate Frizzled revealed that hsmo is 33% homologous to the dSmo sequence reported in Alcedo et al., supra (50% homologous in the transmembrane domains); 23% homologous to the wingless receptor sequence reported in Bhanot et al., supra; and 25% homologous to the vertebrate Frizzled sequence reported in Chan et al., supra. See FIG. 5 for a comparison of the primary sequences of human Smo, rat Smo and Drosophila Smo.

Example 4

Competitive binding, Co-immunoprecipitation, and Cross-linking Assays

Competitive binding, co-immunoprecipitation and cross-linking assays were conducted to characterize physical association or binding between SHH and rSmo, and between certain biologically active forms of SHH and cells expressing rSmo, mPatched, or both rSmo and mPatched.

1. Materials and Methods

Complementary DNAs for rSmo (described in Example 1); dSmo (described in Alcedo et al., supra); Desert HH (described in Echelard et al., supra); and murine Patched (described in Goodrich et al., supra) were cloned into pRK5 vectors, and epitope tags [Flag epitope tag (Kodak/IBI) and Myc epitope tag (9E10 epitope; InVitrogen)] added to the extreme C-terminus by PCR-based mutagenesis.

SHH-N is the biologically active amino terminus portion of SHH [Lee et al., Science, 266:1528–1537 (1994)]. SHH-N was produced as described by Hynes et al., supra. A radiolabeled form of SHH-N, $^{125}$ISHH-N, was employed.

For IgG-SHH-N production, human embryonic kidney 293 cells were transiently transfected with the expression vector encoding SHH-N fused in frame after amino acid residue 198 to the Fc portion of human IgG-gammal.

Cells were maintained in serum-free media (OptiMEM; Gibco BRL) for 48 hours. The media was then collected and concentrated 10-fold using a centricon-10 membrane. Conditioned media was used at a concentration of 2×.

Binding assays were conducted to test binding between cells expressing rSmo or dSmo and (1) epitope tagged SHH-N, (2) an IgG-SHH-N chimera, and (3) an epitope tagged Desert HH.

For visualization of SHH binding, COS-7 cells (Genentech, Inc.) transiently expressing rSmo or mPatched (murine Patched) were exposed to epitope tagged SHH-N (2 hours at 4° C.), washed 4 times with PBS, then fixed and stained with a cy3-conjugated anti-human IgG (Jackson ImmunoResearch) (for IgG-SHH-N) or anti-Flag M2 antibody (Kodak/IBI) (for Flag-tagged SHH-N).

For immunohistochemistry, COS-7 cells transiently transfected with expression constructs were fixed (10 minutes in 2% paraformaldehyde/0.2% Triton-X 100) and stained using monoclonal anti-Flag M2 antibody (IBI) or anti-Myc antibody (InVitrogen), followed by cy3-conjugated anti-mouse IgG (Jackson Immunoresearch).

For cross-linking, cells were resuspended at a density of 1–2×10$^6$/ml in ice-cold L15 media containing 0.1% BSA and 50 pM $^{125}$I-labeled SHH (with or without a 1000-fold excess of unlabeled SHH) and incubated at 4° C. for 2 hr. 10 mM 1-ethyl-3-(3-dimethylaminopropyl) carbodimide HCl and 5 mM N-hydroxysulfosuccinimide (Pierce Chemical) were added to the samples and incubated at room temperature for 30 minutes. The cells were then washed 3 times with 1 ml of PBS. Cells were then lysed in lysis buffer [1% Brij-96 (Sigma), 50 mM Tris, pH 8.0, 150 mM NaCl, 1 mM PMSF, 10 µM aprotinin, 10 µM leupeptin] and the protein complexes were immunoprecipitated with antibodies to the epitope tags as indicated. Immunoprecipitated proteins were resuspended in sample buffer (80 mM Tris-HCl [pH 6.8], 10% [v/v] glycerol, 1% [w/v] SDS, 0.025% Bromphenol Blue, denatured and run on 4% SDS-polyacrylamide gels, which were dried and exposed to film.

For the equilibrium binding analysis, the cells were processed as above, and incubated with 50 pM $^{125}$I-SHH and various concentrations of cold SHH-N (Cold Ligand). The IGOR program was used to determine $K_d$.

2. Results

The results are shown in FIG. 6. No binding of epitope tagged SHH-N, of IgG-SHH-N chimeric protein or of an epitope tagged Desert HH to cells expressing rSmo or dSmo was observed (FIGS. 6a-b and data not shown). This data (and the data described below) indicated that rSmo, acting alone, would not likely be a receptor for SHH or Desert HH. However, it was hypothesized that rSmo is a component in a multi-subunit SHH receptor complex and that the ligand binding function of this receptor complex would be provided by another membrane protein such as Patched.

Binding assays were also conducted to test binding between cells expressing rSmo or murine patched and (1) an epitope tagged SHH and (2) an IgG-SHH-N chimera. The data shows that epitope tagged SHH-N as well as an IgG-SHH-N chimeric protein bind specifically and reversibly to cells expressing the mouse Patched (mPatched) (mPatched is 33% identical to Drosophila Patched) (FIG. 6c-e). Furthermore, only mPatched could be immunoprecipitated by the IgG-SHH-N protein (FIG. 6f) and antibodies to an epitope tagged mPatched readily co-immunoprecipitated $^{125}$I-SHH-N (FIG. 6h) (antibodies to epitope tagged rSmo could not immunoprecipitate $^{125}$I-SHH-N and the IgG-SHH-N chimera did not immunoprecipitate rSmo).

As shown in FIG. 6g, the cross-linking assay of $^{125}$I-SHH-N to cells expressing rSmo or mPatched in the presence or absence of cold SHH-N revealed that $^{125}$I-SHH-N is cross-linked only to mPatched expressing cells.

The competitive binding assay of $^{125}$I-SHH-N and cells expressing mPatched or mPatched plus rSmo also showed that mPatched and SHH-N had a relatively high affinity of interaction (approximate $K_d$ of 460 pM) (FIG. 6i). This corresponds well to the concentrations of SHH-N which are required to elicit biological responses in multiple systems [Fan et al., supra; Hynes et al. supra; Roelink et al., supra]. No binding to cells expressing rSmo alone was observed (data not shown) and there was no increase in binding affinity to mPatched in the presence of rSmo.

Example 5

Co-immunoprecipitation Assays

To determine whether Patched and Smo form or interact in a physical complex, co-immunoprecipitation experiments were performed.

1. Materials and Methods

For the double immunohistochemistry, COS-7 cells transiently transfected with expression constructs were permeabilized using 0.20% Triton-x 100. The cells were fixed (10 minutes in 2% paraformaldehyde/0.2% Triton-X 100) and stained using monoclonal anti-Flag M2 antibody (IBI) and rabbit polyclonal anti-Myc primary antibodies (Santa Cruz Biotech), followed by cy3-conjugated anti-mouse IgG (Jackson Immunoresearch) and bodipy-conjugated anti-rabbit IgG secondary antibodies (Molecular Probes, Inc.).

Human embryonic kidney 293 cells were transiently transfected with expression vectors for epitope tagged rSmo (Flag epitope) and mPatched (Myc epitope) and the resulting proteins complexes were immunoprecipitated with antibody to one of the epitopes and then analyzed on a western blot.

For the co-immunoprecipitation assay, lysates from 293 embryonic kidney cells transiently expressing Flag-tagged rSmo, Myc-tagged mPatched or a combination of the two proteins were incubated (48 hours after transfection) in the presence or absence of the IgG-SHH-N chimera (1 µg/ml, 30 minutes at 37° C.) or in the presence of $^{125}$I-SHH-N with or without an excess of cold SHH-N (2 hours at 4° C.). The incubated samples were then washed 3 times with PBS, and lysed in lysis buffer (see Example 4) as described by Davis et al., Science, 259:1736–1739 (1993). The cell lysates were centrifuged at 10,000 rpm for 10 minutes, and the soluble protein complexes were immunoprecipitated with either protein A sepharose (for the IgG-SHH-N), or anti-Flag or anti-Myc antibodies followed by protein A sepharose (for the epitope-tagged rSmo or mPatched, respectively).

The samples were heated to 100° C. for 5 minutes in denaturing SDS sample buffer (125 mM Tris, pH 6.8, 2% SDS, 10% glycerol, 100 mM b-mercaptoethanol, 0.05% bromphenol blue) and subjected to SDS-PAGE. The proteins were detected either by exposure of the dried gel to film (for $^{125}$I-SHH-N) or by blotting to nitrocellulose and probing with antibodies to Flag or Myc epitopes using the ECL detection system (Amersham).

2. Results

The results are illustrated in FIG. 7. In cells expressing mPatched alone, or rSmo alone, no co-immunoprecipitated protein complexes could be detected. In contrast, in cells that expressed both mPatched and rSmo (FIG. 7a), rSmo was readily co-immunoprecipitated by antibodies to the epitope tagged mPatched (FIG. 7b) and mPatched was co-immunoprecipitated by antibodies to the epitope tagged rSmo (FIG. 7c).

The $^{125}$I-SHH-N was readily co-immunoprecipitated by antibodies to the epitope tagged rSmo or mPatched from cells that expressed both rSmo and mPatched, but not from cells expressing rSmo alone (FIGS. 7d and 7e). These results indicate that SHH-N, rSmo and mPatched are present in the same physical complex, and that a rSmo-SHH complex does not form in the absence of mPatched. Although not fully understood and not being bound by any particular theory, it is believed that Patched is a ligand binding component and vSmo is a signalling component in a multi-subunit SHH receptor (See, FIG. 9). Patched is also believed to be a negative regulator of vSmo.

Example 6

Hahn et al., supra, Johnson et al., supra, and Gailani et al., supra, report that Patched mutations have been associated with BCNS and sporadic basal cell carcinoma ("BCC"). These investigators also report that most of the Patched mutations in BCNS are truncations in which no functional protein is produced. It is believed that BCNS and BCC may be caused or associated with constitutive activation of vSmo, following its release from negative regulation by Patched.

Expression levels of wild-type (native) murine Patched and a mutant Patched were examined. A Patched mutant was generated by site-directed mutagenesis of the wild-type mouse Patched cDNA (described in Example 4) and verified by sequencing. The mutant Patched contained a 3 amino acid insertion (Pro-Asn-Ile) after amino acid residue 815 (this mutant was found in a BCNS family, see, Hahn et al., supra). For analysis of protein expression, equal amounts of pRK5 expression vectors containing wild-type or mutant Patched were transfected into 293 cells, and an equal number of cells (2×10$^6$) were lysed per sample. Proteins were immunoprecipitated from cell lysates by antibody to the Patched epitope tag (myc) and detected on a Western blot with the same antibody.

Applicants found that expression of the mutant Patched (which retains a complete open reading frame) was reduced at least 10-fold as compared to its wild-type counterpart. See FIG. 8.

Deposit of Material

The following materials have been deposited with the American Type Culture Collection, 12801 University Boulevard, Manassas, Va. 20110-2209 USA (ATCC):

| Material | ATCC Dep. No. | Deposit Date |
| --- | --- | --- |
| puc.118.hsmo.5 | 98162 | Sept. 6, 1996 |
| puc.118.hsmo.14 | 98163 | Sept. 6, 1996 |
| pRK5.rsmo.AR140 | 98165 | Sept. 10, 1996 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An antibody which specifically binds to an isolated, vertebrate Smoothened polypeptide, wherein said Smoothened polypeptide is encoded by a nucleic acid which hybridizes to the complement of the nucleic acid sequence of SEQ ID NO:3 under the following conditions: hybridization at 42° C. in 50% formamide, 5×SSC, 10×Denhardt's, 0.05M sodium phosphate (pH 6.5), 0.1% sodium pyrophosnhate, 50 µg/ml sonicated salmon sperm; and rinsing with 2×SSC and washing with 0.5×SSC, 0.1% SDS at 42° C.

2. The antibody of claim 1 wherein said antibody is a monoclonal antibody.

3. An article of manufacture, comprising a container and a composition contained within said container, wherein the composition comprises the vertebrate Smoothened antibody of claim 1 and at least one component selected from the group consisting of a buffer and a diluent.

4. The article of manufacture of claim 3 further comprising a component selected from the group consisting of a filter and instructions for using the antibody in vivo or ex vivo.

5. An antibody which specifically binds to an isolated, vertebrate Smoothened polypeptide, wherein said Smoothened polypeptide is encoded by a nucleic acid which hybridizes to the complement of the nucleic acid sequence of SEQ ID NO:1 under the following conditions: hybridization at 42° C. in 50% formamide, 5×SSC, 10×Denhardt's, 0.05M sodium phosphate (pH 6.5), 0.1% sodium pyrophosphate, 50 µg/ml sonicated salmon sperm; and rinsing with 2×SSC and washing with 0.5×SSC, 0.1% SDS at 42° C.

6. The antibody of claim 5 wherein said antibody is a monoclonal antibody.

7. An article of manufacture, comprising a container and a composition contained within said container, wherein the composition comprising the vertebrate Smoothened antibody of claim 5 and at least one component selected from the group consisting of a buffer and a diluent.

8. The article of manufacture of claim 7 further comprising a component selected from the group consisting of a filter and instructions for using the antibody in vivo or ex vivo.

9. An antibody which binds to the isolated, native sequence vertebrate Smoothened polypeptide of SEQ ID NO:4.

10. An antibody which binds to the isolated, native sequence vertebrate Smoothened polypeptide of SEQ ID NO:2.

11. An antibody which binds to the isolated, vertebrate Smoothened polypeptide encoded by the human nucleic acid deposited under ATCC Dep. No. 98162.

12. An antibody which binds to the isolated, vertebrate Smoothened polypeptide encoded by the human nucleic acid deposited under ATCC Dep. No. 98163.

13. An antibody which binds to the isolated, vertebrate Smoothened polypeptide encoded by the human nucleic acid deposited under ATCC Dep. No. 98165.

* * * * *

UNITED STATES PATENT AND TRADEMARK OFFICE
CERTIFICATE OF CORRECTION

PATENT NO. : 6,136,958
DATED : October 24, 2000
INVENTOR(S) : de Sauvage et al.

It is certified that error appears in the above-identified patent and that said Letters Patent is hereby corrected as shown below:

Column 3,
Line 34, delete "smo" and insert therefor -- Smo --.

Column 5,
Line 13, delete "wil" and insert therefor -- will --.

Column 16,
Line 5, delete "as".

Column 17,
Line 53, delete "-tubulin" and insert therefor -- α-tubulin --.

Column 18,
Line 61, delete "vsmo" and insert therefor -- vSmo --.

Column 20,
Line 1, delete "vsmo" and insert therefor -- vSmo --.
Line 43, delete "immunoabsorbent" and insert therefor -- immunoasorbent --

Column 26,
Line 6, delete "100" and insert therefor -- 100% --.
Line 31, delete "1.2x106" and insert therefor -- $1.2 \times 10^6$ --.

Column 27,
Line 56, delte "(indian HH)" and insert therefor -- (Indian HH) --.

UNITED STATES PATENT AND TRADEMARK OFFICE
CERTIFICATE OF CORRECTION

PATENT NO.   : 6,136,958
DATED        : October 24, 2000
INVENTOR(S)  : de Sauvage et al.

It is certified that error appears in the above-identified patent and that said Letters Patent is hereby corrected as shown below:

Column 30,
Line 64, delete "b-mercaptoethanol" and insert therefor -- β-mercaptoethanol --.

Claim 1,
Line 49, delete "pyrophosnhate" and insert therefore -- pyrophosphate --.

Signed and Sealed this

Twenty-third Day of October, 2001

Attest:

*Nicholas P. Godici*

NICHOLAS P. GODICI
*Attesting Officer*       *Acting Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 3854 base pairs
      (B) TYPE: Nucleic Acid
      (C) STRANDEDNESS: Single (D) TOPOLOGY: Linear (xi) SEQUENCE DESCRIPTION: SEQ ID NO:1:

```
GCGGCGCGCT CGCGCGGAGG TGGCTGCTGG GCCGCGGGCT GGCGTGGGGG              50

CGGAGCCGGG GAGCGACTCC CGCACCCCAC GGCCGGTGCC TGCCCTCCAT             100

CGAGGGGCTG GGAGTTAGTT TTAATGGTGG GAGAGGGAAT GGGGCTGAAG             150

ATCGGGGCCC CAGAGGGTTC CCAGGGTTGA AGACAATTCC AATCGAGGCG             200

AGGGAGTCCG GGGTCCGTGC ATCCTGGCCC GGGCCTGCGC AGCTCAACAT             250

GGGGCCCGGG TTCCAAAGTT TGCAAAGTTG GGAGCCGAGG GGCCCGGACG             300

CGCGCGGCGC CTGGCGAAAG CTGGCCCCAG ACTTTCGGGG CGCACCGGTC             350

GCCTAAGTAG CCTCCGCGGC CCCCGGGGTC GTGTGTGTGG CCAGGGGACT             400

CCGGGGAGCT CGGGGCGCC TCAGCTTCTG CTGAGTTGGC GGTTTGGCC               449
```

| | | | | |
|---|---|---|---|---|
| ATG GCT GCT GGC CGC CCC GTG CGT GGG CCC GAG CTG GCG | | | | | 488 |
| Met Ala Ala Gly Arg Pro Val Arg Gly Pro Glu Leu Ala | | | | | |
| 1 5 10 | | | | | |

```
CCC CGG AGG CTG CTG CAG TTG CTG CTG CTG GTA CTG CTT              527
Pro Arg Arg Leu Leu Gln Leu Leu Leu Leu Val Leu Leu
         15              20               25

GGG GGC CGG GGC CGG GGG GCG GCC TTG AGC GGG AAC GTG              566
Gly Gly Arg Gly Arg Gly Ala Ala Leu Ser Gly Asn Val
              30               35

ACC GGG CCT GGG CCT CGC AGT GCC GGC GGG AGC GCG AGG              605
Thr Gly Pro Gly Pro Arg Ser Ala Gly Gly Ser Ala Arg
 40              45                    50

AGG AAC GCG CCG GTG ACC AGC CCT CCG CCG CCG CTG CTG              644
Arg Asn Ala Pro Val Thr Ser Pro Pro Pro Pro Leu Leu
         55                   60               65

AGC CAC TGC GGC CGG GCC GCC CAC TGC GAG CCT TTG CGC              683
Ser His Cys Gly Arg Ala Ala His Cys Glu Pro Leu Arg
              70               75

TAC AAC GTG TGC CTG GGC TCC GCG CTG CCC TAC GGA GCC              722
Tyr Asn Val Cys Leu Gly Ser Ala Leu Pro Tyr Gly Ala
 80                   85                    90

ACC ACC ACG CTG CTG GCT GGG GAC TCG GAC TCG CAG GAG              761
Thr Thr Thr Leu Leu Ala Gly Asp Ser Asp Ser Gln Glu
              95                  100

GAA GCG CAC AGC AAG CTC GTG CTC TGG TCC GGC CTC CGG              800
Glu Ala His Ser Lys Leu Val Leu Trp Ser Gly Leu Arg
105                  110                  115

AAT GCT CCC CGA TGC TGG GCA GTG ATC CAG CCC CTG CTG              839
Asn Ala Pro Arg Cys Trp Ala Val Ile Gln Pro Leu Leu
              120                  125                  130

TGT GCT GTC TAC ATG CCC AAG TGT GAA AAT GAC CGA GTG              878
Cys Ala Val Tyr Met Pro Lys Cys Glu Asn Asp Arg Val
                   135                  140

GAG TTG CCC AGC CGT ACC CTC TGC CAG GCC ACC CGA GGC              917
Glu Leu Pro Ser Arg Thr Leu Cys Gln Ala Thr Arg Gly
145                  150                       155

CCC TGT GCC ATT GTG GAG CGG GAA CGA GGG TGG CCT GAC              956
Pro Cys Ala Ile Val Glu Arg Glu Arg Gly Trp Pro Asp
              160                       165

TTT CTG CGT TGC ACG CCG GAC CAC TTC CCT GAA GGC TGT              995
Phe Leu Arg Cys Thr Pro Asp His Phe Pro Glu Gly Cys
170                  175                       180
```

-continued

```
CCA AAC GAG GTA CAA AAC ATC AAG TTC AAC AGT TCA GGC          1034
Pro Asn Glu Val Gln Asn Ile Lys Phe Asn Ser Ser Gly
    185                 190                 195

CAA TGT GAA GCA CCC TTG GTG AGG ACA GAC AAC CCC AAG          1073
Gln Cys Glu Ala Pro Leu Val Arg Thr Asp Asn Pro Lys
            200                 205

AGC TGG TAC GAG GAC GTG GAG GGC TGT GGG ATC CAG TGC          1112
Ser Trp Tyr Glu Asp Val Glu Gly Cys Gly Ile Gln Cys
    210                 215                 220

CAG AAC CCG CTG TTC ACC GAG GCT GAG CAC CAG GAC ATG          1151
Gln Asn Pro Leu Phe Thr Glu Ala Glu His Gln Asp Met
            225                 230

CAC AGT TAC ATC GCA GCC TTC GGG GCG GTC ACC GGC CTC          1190
His Ser Tyr Ile Ala Ala Phe Gly Ala Val Thr Gly Leu
235                 240                 245

TGT ACA CTC TTC ACC CTG GCC ACC TTT GTG GCT GAC TGG          1229
Cys Thr Leu Phe Thr Leu Ala Thr Phe Val Ala Asp Trp
            250                 255                 260

CGG AAC TCC AAT CGC TAC CCT GCG GTT ATT CTC TTC TAT          1268
Arg Asn Ser Asn Arg Tyr Pro Ala Val Ile Leu Phe Tyr
                265                 270

GTC AAT GCG TGT TTC TTT GTG GGC AGC ATT GGC TGG CTG          1307
Val Asn Ala Cys Phe Phe Val Gly Ser Ile Gly Trp Leu
275                 280                 285

GCC CAG TTC ATG GAT GGT GCC CGC CGG GAG ATT GTT TGC          1346
Ala Gln Phe Met Asp Gly Ala Arg Arg Glu Ile Val Cys
            290                 295

CGA GCA GAT GGC ACC ATG AGA TTT GGG GAG CCC ACC TCC          1385
Arg Ala Asp Gly Thr Met Arg Phe Gly Glu Pro Thr Ser
300                 305                 310

AGC GAG ACC CTA TCC TGT GTC ATC ATT TTT GTC ATC GTG          1424
Ser Glu Thr Leu Ser Cys Val Ile Ile Phe Val Ile Val
            315                 320                 325

TAC TAT GCC TTG ATG GCT GGA GTA GTG TGG TTC GTG GTC          1463
Tyr Tyr Ala Leu Met Ala Gly Val Val Trp Phe Val Val
                330                 335

CTC ACC TAT GCC TGG CAC ACC TCC TTC AAA GCC CTG GGC          1502
Leu Thr Tyr Ala Trp His Thr Ser Phe Lys Ala Leu Gly
    340                 345                 350

ACC ACT TAC CAG CCT CTC TCG GGC AAG ACA TCC TAT TTC          1541
Thr Thr Tyr Gln Pro Leu Ser Gly Lys Thr Ser Tyr Phe
            355                 360

CAC CTG CTC ACG TGG TCA CTC CCC TTC GTC CTC ACT GTG          1580
His Leu Leu Thr Trp Ser Leu Pro Phe Val Leu Thr Val
365                 370                 375

GCA ATC CTT GCT GTG GCT CAG GTA GAT GGG GAC TCC GTG          1619
Ala Ile Leu Ala Val Ala Gln Val Asp Gly Asp Ser Val
            380                 385                 390

AGT GGC ATC TGC TTT GTA GGC TAC AAG AAC TAT CGG TAC          1658
Ser Gly Ile Cys Phe Val Gly Tyr Lys Asn Tyr Arg Tyr
                395                 400

CGT GCT GGC TTT GTA CTT GCC CCA ATT GGC CTG GTG CTT          1697
Arg Ala Gly Phe Val Leu Ala Pro Ile Gly Leu Val Leu
    405                 410                 415

ATT GTG GGA GGC TAC TTC CTC ATC CGA GGG GTC ATG ACT          1736
Ile Val Gly Gly Tyr Phe Leu Ile Arg Gly Val Met Thr
                420                 425

CTG TTC TCC ATC AAG AGC AAC CAC CCT GGG CTT CTG AGT          1775
Leu Phe Ser Ile Lys Ser Asn His Pro Gly Leu Leu Ser
430                 435                 440
```

```
GAG AAG GCA GCC AGC AAG ATC AAT GAG ACC ATG CTG CGC            1814
Glu Lys Ala Ala Ser Lys Ile Asn Glu Thr Met Leu Arg
            445                 450                 455

CTG GGC ATT TTT GGC TTC CTC GCC TTT GGC TTC GTG CTC            1853
Leu Gly Ile Phe Gly Phe Leu Ala Phe Gly Phe Val Leu
            460                 465

ATC ACC TTC AGC TGC CAC TTC TAT GAC TTC TTC AAC CAG            1892
Ile Thr Phe Ser Cys His Phe Tyr Asp Phe Phe Asn Gln
            470                 475                 480

GCT GAG TGG GAG CGT AGC TTC CGG GAC TAT GTG CTA TGC            1931
Ala Glu Trp Glu Arg Ser Phe Arg Asp Tyr Val Leu Cys
            485                 490

CAA GCC AAT GTG ACC ATT GGG CTG CCT ACC AAG AAG CCC            1970
Gln Ala Asn Val Thr Ile Gly Leu Pro Thr Lys Lys Pro
495                 500                 505

ATT CCT GAT TGT GAG ATC AAG AAT CGG CCC AGC CTC CTG            2009
Ile Pro Asp Cys Glu Ile Lys Asn Arg Pro Ser Leu Leu
            510                 515                 520

GTG GAG AAG ATC AAT CTG TTT GCC ATG TTT GGC ACT GGC            2048
Val Glu Lys Ile Asn Leu Phe Ala Met Phe Gly Thr Gly
            525                 530

ATT GCC ATG AGC ACC TGG GTC TGG ACC AAG GCC ACC CTG            2087
Ile Ala Met Ser Thr Trp Val Trp Thr Lys Ala Thr Leu
            535                 540                 545

CTC ATC TGG AGG CGC ACC TGG TGC AGG TTG ACT GGG CAC            2126
Leu Ile Trp Arg Arg Thr Trp Cys Arg Leu Thr Gly His
            550                 555

AGT GAT GAT GAA CCC AAG AGA ATC AAG AAA AGC AAG ATG            2165
Ser Asp Asp Glu Pro Lys Arg Ile Lys Lys Ser Lys Met
560                 565                 570

ATT GCC AAG GCC TTC TCT AAG CGG CGT GAA CTG CTG CAG            2204
Ile Ala Lys Ala Phe Ser Lys Arg Arg Glu Leu Leu Gln
            575                 580                 585

AAC CCG GGC CAG GAG CTC TCC TTC AGC ATG CAC ACT GTC            2243
Asn Pro Gly Gln Glu Leu Ser Phe Ser Met His Thr Val
                    590                 595

TCC CAT GAT GGA CCT GTT GCC GGT TTG GCT TTT GAA CTC            2282
Ser His Asp Gly Pro Val Ala Gly Leu Ala Phe Glu Leu
            600                 605                 610

AAT GAA CCC TCA GCT GAT GTC TCC TCT GCC TGG GCC CAG            2321
Asn Glu Pro Ser Ala Asp Val Ser Ser Ala Trp Ala Gln
            615                 620

CAC GTC ACC AAG ATG GTG GCT CGA AGA GGA GCC ATA TTA            2360
His Val Thr Lys Met Val Ala Arg Arg Gly Ala Ile Leu
625                 630                 635

CCC CAG GAT GTG TCT GTC ACC CCT GTG GCA ACT CCA GTG            2399
Pro Gln Asp Val Ser Val Thr Pro Val Ala Thr Pro Val
            640                 645                 650

CCA CCA GAA GAA CAA GCC AAC CTG TGG CTG GTT GAG GCA            2438
Pro Pro Glu Glu Gln Ala Asn Leu Trp Leu Val Glu Ala
                    655                 660

GAG ATC TCC CCA GAG TTA GAG AAG CGT TTA GGC CGG AAG            2477
Glu Ile Ser Pro Glu Leu Glu Lys Arg Leu Gly Arg Lys
            665                 670                 675

AAG AAG CGG AGG AAG AGG AAG AAG GAG GTG TGC CCC TTG            2516
Lys Lys Arg Arg Lys Arg Lys Lys Glu Val Cys Pro Leu
                    680                 685

GGG CCA GCC CCT GAA CTT CAC CAC TCT GCC CCT GTT CCT            2555
Gly Pro Ala Pro Glu Leu His His Ser Ala Pro Val Pro
690                 695                 700
```

```
GCC ACC AGT GCA GTT CCT CGG CTG CCT CAG CTG CCT CGG         2594
Ala Thr Ser Ala Val Pro Arg Leu Pro Gln Leu Pro Arg
        705                 710                 715

CAG AAG TGC CTA GTA GCT GCA AAT GCC TGG GGA ACA GGA         2633
Gln Lys Cys Leu Val Ala Ala Asn Ala Trp Gly Thr Gly
            720                 725

GAG CCC TGC CGA CAG GGA GCC TGG ACT GTA GTC TCC AAC         2672
Glu Pro Cys Arg Gln Gly Ala Trp Thr Val Val Ser Asn
    730                 735                 740

CCC TTC TGC CCA GAG CCT AGT CCC CAT CAA GAT CCA TTT         2711
Pro Phe Cys Pro Glu Pro Ser Pro His Gln Asp Pro Phe
                745                 750

CTC CCT GGT GCC TCA GCC CCC AGG GTC TGG GCT CAG GGC         2750
Leu Pro Gly Ala Ser Ala Pro Arg Val Trp Ala Gln Gly
755                 760                 765

CGC CTC CAG GGG CTG GGA TCC ATT CAT TCC CGC ACT AAC         2789
Arg Leu Gln Gly Leu Gly Ser Ile His Ser Arg Thr Asn
        770                 775                 780

CTA ATG GAG GCT GAG CTC TTG GAT GCA GAC TCG GAC TTC TG      2830
Leu Met Glu Ala Glu Leu Leu Asp Ala Asp Ser Asp Phe
            785                 790         793

AGCTTGCAGG GCAGGTCCTA GGATGGGGAA GACAAGTGCA CGCCTTCCTA      2880

TAGCTCTTCC TGAGAGCACA CCTCTGGGGT CTCATCTGAC AGTCTATGGG      2930

CCATGTATCT GCCTACAAGA GCTGTGTACG ACTGGCTAGA AGCAGCCAGA      2980

CCATAGAAAC AAGCTGAACA CAGCCACTGA TAGACCTCAC TTCAGAAGCA      3030

AGACCTGCAG TTCAGGACCC TTGCCTCTGC CCCCCAATTA GAGTCTGGCT      3080

GGCAGTGTTA GTCTCCAACA GAGCTTGTAC TAGGGTAGGA ACGGCAGAGG      3130

CAGGGGTGAT GGTACCCAGA GTGGGCTGGG GTGTCCAGTG AGGTAACCAA      3180

GCCCATGTCT GGCAGATGAG GGCTGGCTGC CCTTTTCTGT GCCAATGAGT      3230

GCCCTTTTCT GGCGCTCTGA GACCAAAAGT GTTTATTGTG TCATTTGTCC      3280

TTTTTCTAGG TGGGAACAGG ACTCTCTTTT TCCTCTTCCT GGTAGTTGTA      3330

ATGACTACTC CCATAAGGCC TAGAACTGCT CTCAGTAGGT GGCCCTGTCC      3380

AAAACACATC TTCACATCTT AGTTCCACTA GGCCAAACTC TTATTGGTTA      3430

GCACCTTAAA ACACACACAC ACACACACAC ACACACACAC ACACACACAC      3480

ACACACACAC ACCCTCTTAC TTCTGAGCTT GGTCTCAAGA GAGAGACAAC      3530

TGGTTCAGCT CCAGGCCTCT GAGAGTCATG TTTTCTTCCT CACATCCATC      3580

CAGTGGGGAT GGATCCTCTG ACTTAAGGGG CTACCTTGGG AAGCCTCTGT      3630

AGCTTCAGCC AGGCAAGAAA GCTTCTTCCA ACTTCTGTAT CTGGTGGGAA      3680

GGAGGACTCC CTACTTTTTA CAATGTCTAG TCATTTTCAT AGTGCCCCAC      3730

ATTCAAGAAC CAGACAGCAG GATGCCTTAG AAGCTGGCTG GGTTCCAGGT      3780

CAGAGGCTCA GTATGAGAAG AAGAAATATG AACAGTAAAT AAAACATTTT      3830

TGTATAAAAA AAAAAAAAAA AAAA                                 3854

(2) INFORMATION FOR SEQ ID NO:2:

(i) SEQUENCE CHARACTERISTICS:
        (A) LENGTH: 793 amino acids
        (B) TYPE: Amino Acid
        (D) TOPOLOGY: Linear
```

-continued (xi) SEQUENCE DESCRIPTION: SEQ ID NO:2:

```
Met Ala Gly Arg Pro Val Arg Gly Pro Glu Leu Ala Pro Arg
 1               5                  10                  15
Arg Leu Leu Gln Leu Leu Leu Val Leu Leu Gly Gly Arg Gly
                20                  25                  30
Arg Gly Ala Ala Leu Ser Gly Asn Val Thr Gly Pro Gly Pro Arg
                35                  40                  45
Ser Ala Gly Gly Ser Ala Arg Arg Asn Ala Pro Val Thr Ser Pro
                50                  55                  60
Pro Pro Pro Leu Leu Ser His Cys Gly Arg Ala Ala His Cys Glu
                65                  70                  75
Pro Leu Arg Tyr Asn Val Cys Leu Gly Ser Ala Leu Pro Tyr Gly
                80                  85                  90
Ala Thr Thr Thr Leu Leu Ala Gly Asp Ser Asp Ser Gln Glu Glu
                95                 100                 105
Ala His Ser Lys Leu Val Leu Trp Ser Gly Leu Arg Asn Ala Pro
               110                 115                 120
Arg Cys Trp Ala Val Ile Gln Pro Leu Leu Cys Ala Val Tyr Met
               125                 130                 135
Pro Lys Cys Glu Asn Asp Arg Val Glu Leu Pro Ser Arg Thr Leu
               140                 145                 150
Cys Gln Ala Thr Arg Gly Pro Cys Ala Ile Val Glu Arg Glu Arg
               155                 160                 165
Gly Trp Pro Asp Phe Leu Arg Cys Thr Pro Asp His Phe Pro Glu
               170                 175                 180
Gly Cys Pro Asn Glu Val Gln Asn Ile Lys Phe Asn Ser Ser Gly
               185                 190                 195
Gln Cys Glu Ala Pro Leu Val Arg Thr Asp Asn Pro Lys Ser Trp
               200                 205                 210
Tyr Glu Asp Val Glu Gly Cys Gly Ile Gln Cys Gln Asn Pro Leu
               215                 220                 225
Phe Thr Glu Ala Glu His Gln Asp Met His Ser Tyr Ile Ala Ala
               230                 235                 240
Phe Gly Ala Val Thr Gly Leu Cys Thr Leu Phe Thr Leu Ala Thr
               245                 250                 255
Phe Val Ala Asp Trp Arg Asn Ser Asn Arg Tyr Pro Ala Val Ile
               260                 265                 270
Leu Phe Tyr Val Asn Ala Cys Phe Phe Val Gly Ser Ile Gly Trp
               275                 280                 285
Leu Ala Gln Phe Met Asp Gly Ala Arg Arg Glu Ile Val Cys Arg
               290                 295                 300
Ala Asp Gly Thr Met Arg Phe Gly Glu Pro Thr Ser Ser Glu Thr
               305                 310                 315
Leu Ser Cys Val Ile Ile Phe Val Ile Val Tyr Tyr Ala Leu Met
               320                 325                 330
Ala Gly Val Val Trp Phe Val Val Leu Thr Tyr Ala Trp His Thr
               335                 340                 345
Ser Phe Lys Ala Leu Gly Thr Thr Tyr Gln Pro Leu Ser Gly Lys
               350                 355                 360
Thr Ser Tyr Phe His Leu Leu Thr Trp Ser Leu Pro Phe Val Leu
               365                 370                 375
Thr Val Ala Ile Leu Ala Val Ala Gln Val Asp Gly Asp Ser Val
               380                 385                 390
```

```
Ser Gly Ile Cys Phe Val Gly Tyr Lys Asn Tyr Arg Tyr Arg Ala
            395                 400                 405

Gly Phe Val Leu Ala Pro Ile Gly Leu Val Leu Ile Val Gly Gly
            410                 415                 420

Tyr Phe Leu Ile Arg Gly Val Met Thr Leu Phe Ser Ile Lys Ser
            425                 430                 435

Asn His Pro Gly Leu Leu Ser Glu Lys Ala Ala Ser Lys Ile Asn
            440                 445                 450

Glu Thr Met Leu Arg Leu Gly Ile Phe Gly Phe Leu Ala Phe Gly
            455                 460                 465

Phe Val Leu Ile Thr Phe Ser Cys His Phe Tyr Asp Phe Phe Asn
            470                 475                 480

Gln Ala Glu Trp Glu Arg Ser Phe Arg Asp Tyr Val Leu Cys Gln
            485                 490                 495

Ala Asn Val Thr Ile Gly Leu Pro Thr Lys Lys Pro Ile Pro Asp
            500                 505                 510

Cys Glu Ile Lys Asn Arg Pro Ser Leu Leu Val Glu Lys Ile Asn
            515                 520                 525

Leu Phe Ala Met Phe Gly Thr Gly Ile Ala Met Ser Thr Trp Val
            530                 535                 540

Trp Thr Lys Ala Thr Leu Leu Ile Trp Arg Arg Thr Trp Cys Arg
            545                 550                 555

Leu Thr Gly His Ser Asp Asp Glu Pro Lys Arg Ile Lys Lys Ser
            560                 565                 570

Lys Met Ile Ala Lys Ala Phe Ser Lys Arg Arg Glu Leu Leu Gln
            575                 580                 585

Asn Pro Gly Gln Glu Leu Ser Phe Ser Met His Thr Val Ser His
            590                 595                 600

Asp Gly Pro Val Ala Gly Leu Ala Phe Glu Leu Asn Glu Pro Ser
            605                 610                 615

Ala Asp Val Ser Ser Ala Trp Ala Gln His Val Thr Lys Met Val
            620                 625                 630

Ala Arg Arg Gly Ala Ile Leu Pro Gln Asp Val Ser Val Thr Pro
            635                 640                 645

Val Ala Thr Pro Val Pro Pro Glu Gln Ala Asn Leu Trp Leu
            650                 655                 660

Val Glu Ala Glu Ile Ser Pro Glu Leu Glu Lys Arg Leu Gly Arg
            665                 670                 675

Lys Lys Lys Arg Arg Lys Arg Lys Glu Val Cys Pro Leu Gly
            680                 685                 690

Pro Ala Pro Glu Leu His His Ser Ala Pro Val Pro Ala Thr Ser
            695                 700                 705

Ala Val Pro Arg Leu Pro Gln Leu Pro Arg Gln Lys Cys Leu Val
            710                 715                 720

Ala Ala Asn Ala Trp Gly Thr Gly Glu Pro Cys Arg Gln Gly Ala
            725                 730                 735

Trp Thr Val Val Ser Asn Pro Phe Cys Pro Glu Pro Ser Pro His
            740                 745                 750

Gln Asp Pro Phe Leu Pro Gly Ala Ser Ala Pro Arg Val Trp Ala
            755                 760                 765
```

Gln Gly Arg Leu Gln Gly Leu Gly Ser Ile His Ser Arg Thr Asn
            770                 775                 780

Leu Met Glu Ala Glu Leu Leu Asp Ala Asp Ser Asp Phe
            785                 790         793

(2) INFORMATION FOR SEQ ID NO:3:

(i) SEQUENCE CHARACTERISTICS:
        (A) LENGTH: 2972 base pairs
        (B) TYPE: Nucleic Acid
        (C) STRANDEDNESS: Single
        (D) TOPOLOGY: Linear (xi) SEQUENCE DESCRIPTION: SEQ ID NO:3:

| | |
|---|---|
| CGGGGGTTGG CC  ATG GCC GCT GCC CGC CCA GCG CGG GGG<br>                Met Ala Ala Ala Arg Pro Ala Arg Gly<br>                 1               5 | 39 |
| CCG GAG CTC CCG CTC CTG GGG CTG CTG CTG CTG CTG<br>Pro Glu Leu Pro Leu Leu Gly Leu Leu Leu Leu Leu<br>10              15                  20 | 78 |
| CTG GGG GAC CCG GGC CGG GGG GCG GCC TCG AGC GGG AAC<br>Leu Gly Asp Pro Gly Arg Gly Ala Ala Ser Ser Gly Asn<br>        25              30              35 | 117 |
| GCG ACC GGG CCT GGG CCT CGG AGC GCG GGC GGG AGC GCG<br>Ala Thr Gly Pro Gly Pro Arg Ser Ala Gly Gly Ser Ala<br>            40              45 | 156 |
| AGG AGG AGC GCG GCG GTG ACT GGC CCT CCG CCG CCG CTG<br>Arg Arg Ser Ala Ala Val Thr Gly Pro Pro Pro Pro Leu<br>50              55              60 | 195 |
| AGC CAC TGC GGC CGG GCT GCC CCC TGC GAG CCG CTG CGC<br>Ser His Cys Gly Arg Ala Ala Pro Cys Glu Pro Leu Arg<br>            65              70 | 234 |
| TAC AAC GTG TGC CTG GGC TCG GTG CTG CCC TAC GGG GCC<br>Tyr Asn Val Cys Leu Gly Ser Val Leu Pro Tyr Gly Ala<br>75              80              85 | 273 |
| ACC TCC ACA CTG CTG GCC GGA GAC TCG GAC TCC CAG GAG<br>Thr Ser Thr Leu Leu Ala Gly Asp Ser Asp Ser Gln Glu<br>        90              95              100 | 312 |
| GAA GCG CAC GGC AAG CTC GTG CTC TGG TCG GGC CTC CGG<br>Glu Ala His Gly Lys Leu Val Leu Trp Ser Gly Leu Arg<br>            105             110 | 351 |
| AAT GCC CCC CGC TGC TGG GCA GTG ATC CAG CCC CTG CTG<br>Asn Ala Pro Arg Cys Trp Ala Val Ile Gln Pro Leu Leu<br>115             120             125 | 390 |
| TGT GCC GTA TAC ATG CCC AAG TGT GAG AAT GAC CGG GTG<br>Cys Ala Val Tyr Met Pro Lys Cys Glu Asn Asp Arg Val<br>        130             135 | 429 |
| GAG CTG CCC AGC CGT ACC CTC TGC CAG GCC ACC CGA GGC<br>Glu Leu Pro Ser Arg Thr Leu Cys Gln Ala Thr Arg Gly<br>140             145             150 | 468 |
| CCC TGT GCC ATC GTG GAG AGG GAG CGG GGC TGG CCT GAC<br>Pro Cys Ala Ile Val Glu Arg Glu Arg Gly Trp Pro Asp<br>        155             160             165 | 507 |
| TTC CTG CGC TGC ACT CCT GAC CGC TTC CCT GAA GGC TGC<br>Phe Leu Arg Cys Thr Pro Asp Arg Phe Pro Glu Gly Cys<br>            170             175 | 546 |
| ACG AAT GAG GTG CAG AAC ATC AAG TTC AAC AGT TCA GGC<br>Thr Asn Glu Val Gln Asn Ile Lys Phe Asn Ser Ser Gly<br>        180             185             190 | 585 |

-continued

| | |
|---|---|
| CAG TGC GAA GTG CCC TTG GTT CGG ACA GAC AAC CCC AAG<br>Gln Cys Glu Val Pro Leu Val Arg Thr Asp Asn Pro Lys<br>          195                      200 | 624 |
| AGC TGG TAC GAG GAC GTG GAG GGC TGC GGC ATC CAG TGC<br>Ser Trp Tyr Glu Asp Val Glu Gly Cys Gly Ile Gln Cys<br>205                   210                 215 | 663 |
| CAG AAC CCG CTC TTC ACA GAG GCT GAG CAC CAG GAC ATG<br>Gln Asn Pro Leu Phe Thr Glu Ala Glu His Gln Asp Met<br>          220                   225            230 | 702 |
| CAC AGC TAC ATC GCG GCC TTC GGG GCC GTC ACG GGC CTC<br>His Ser Tyr Ile Ala Ala Phe Gly Ala Val Thr Gly Leu<br>                235                    240 | 741 |
| TGC ACG CTC TTC ACC CTG GCC ACA TTC GTG GCT GAC TGG<br>Cys Thr Leu Phe Thr Leu Ala Thr Phe Val Ala Asp Trp<br>245                   250                 255 | 780 |
| CGG AAC TCG AAT CGC TAC CCT GCT GTT ATT CTC TTC TAC<br>Arg Asn Ser Asn Arg Tyr Pro Ala Val Ile Leu Phe Tyr<br>          260                   265 | 819 |
| GTC AAT GCG TGC TTC TTT GTG GGC AGC ATT GGC TGG CTG<br>Val Asn Ala Cys Phe Phe Val Gly Ser Ile Gly Trp Leu<br>270                   275                 280 | 858 |
| GCC CAG TTC ATG GAT GGT GCC CGC CGA GAG ATC GTC TGC<br>Ala Gln Phe Met Asp Gly Ala Arg Arg Glu Ile Val Cys<br>          285                   290           295 | 897 |
| CGT GCA GAT GGC ACC ATG AGG CTT GGG GAG CCC ACC TCC<br>Arg Ala Asp Gly Thr Met Arg Leu Gly Glu Pro Thr Ser<br>                300                    305 | 936 |
| AAT GAG ACT CTG TCC TGC GTC ATC ATC TTT GTC ATC GTG<br>Asn Glu Thr Leu Ser Cys Val Ile Ile Phe Val Ile Val<br>310                   315                 320 | 975 |
| TAC TAC GCC CTG ATG GCT GGT GTG GTT TGG TTT GTG GTC<br>Tyr Tyr Ala Leu Met Ala Gly Val Val Trp Phe Val Val<br>          325                   330 | 1014 |
| CTC ACC TAT GCC TGG CAC ACT TCC TTC AAA GCC CTG GGC<br>Leu Thr Tyr Ala Trp His Thr Ser Phe Lys Ala Leu Gly<br>335                   340                 345 | 1053 |
| ACC ACC TAC CAG CCT CTC TCG GGC AAG ACC TCC TAC TTC<br>Thr Thr Tyr Gln Pro Leu Ser Gly Lys Thr Ser Tyr Phe<br>          350                   355            360 | 1092 |
| CAC CTG CTC ACC TGG TCA CTC CCC TTT GTC CTC ACT GTG<br>His Leu Leu Thr Trp Ser Leu Pro Phe Val Leu Thr Val<br>                365                    370 | 1131 |
| GCA ATC CTT GCT GTG GCG CAG GTG GAT GGG GAC TCT GTG<br>Ala Ile Leu Ala Val Ala Gln Val Asp Gly Asp Ser Val<br>375                   380                 385 | 1170 |
| AGT GGC ATT TGT TTT GTG GGC TAC AAG AAC TAC CGA TAC<br>Ser Gly Ile Cys Phe Val Gly Tyr Lys Asn Tyr Arg Tyr<br>          390                   395 | 1209 |
| CGT GCG GGC TTC GTG CTG GCC CCA ATC GGC CTG GTG CTC<br>Arg Ala Gly Phe Val Leu Ala Pro Ile Gly Leu Val Leu<br>400                   405                 410 | 1248 |
| ATC GTG GGA GGC TAC TTC CTC ATC CGA GGA GTC ATG ACT<br>Ile Val Gly Gly Tyr Phe Leu Ile Arg Gly Val Met Thr<br>          415                   420            425 | 1287 |
| CTG TTC TCC ATC AAG AGC AAC CAC CCC GGG CTG CTG AGT<br>Leu Phe Ser Ile Lys Ser Asn His Pro Gly Leu Leu Ser<br>                430                    435 | 1326 |
| GAG AAG GCT GCC AGC AAG ATC AAC GAG ACC ATG CTG CGC<br>Glu Lys Ala Ala Ser Lys Ile Asn Glu Thr Met Leu Arg<br>440                   445                 450 | 1365 |

```
CTG GGC ATT TTT GGC TTC CTG GCC TTT GGC TTT GTG CTC          1404
Leu Gly Ile Phe Gly Phe Leu Ala Phe Gly Phe Val Leu
            455                 460

ATT ACC TTC AGC TGC CAC TTC TAC GAC TTC TTC AAC CAG          1443
Ile Thr Phe Ser Cys His Phe Tyr Asp Phe Phe Asn Gln
465                 470                 475

GCT GAG TGG GAG CGC AGC TTC CGG GAC TAT GTG CTA TGT          1482
Ala Glu Trp Glu Arg Ser Phe Arg Asp Tyr Val Leu Cys
        480                 485                 490

CAG GCC AAT GTG ACC ATC GGG CTG CCC ACC AAG CAG CCC          1521
Gln Ala Asn Val Thr Ile Gly Leu Pro Thr Lys Gln Pro
                495                 500

ATC CCT GAC TGT GAG ATC AAG AAT CGC CCG AGC CTT CTG          1560
Ile Pro Asp Cys Glu Ile Lys Asn Arg Pro Ser Leu Leu
505                 510                 515

GTG GAG AAG ATC AAC CTG TTT GCC ATG TTT GGA ACT GGC          1599
Val Glu Lys Ile Asn Leu Phe Ala Met Phe Gly Thr Gly
        520                 525

ATC GCC ATG AGC ACC TGG GTC TGG ACC AAG GCC ACG CTG          1638
Ile Ala Met Ser Thr Trp Val Trp Thr Lys Ala Thr Leu
530                 535                 540

CTC ATC TGG AGG CGT ACC TGG TGC AGG TTG ACT GGG CAG          1677
Leu Ile Trp Arg Arg Thr Trp Cys Arg Leu Thr Gly Gln
            545                 550                 555

AGT GAC GAT GAG CCA AAG CGG ATC AAG AAG AGC AAG ATG          1716
Ser Asp Asp Glu Pro Lys Arg Ile Lys Lys Ser Lys Met
                560                 565

ATT GCC AAG GCC TTC TCT AAG CGG CAC GAG CTC CTG CAG          1755
Ile Ala Lys Ala Phe Ser Lys Arg His Glu Leu Leu Gln
570                 575                 580

AAC CCA GGC CAG GAG CTG TCC TTC AGC ATG CAC ACT GTG          1794
Asn Pro Gly Gln Glu Leu Ser Phe Ser Met His Thr Val
        585                 590

TCC CAC GAC GGG CCC GTG GCG GGC TTG GCC TTT GAC CTC          1833
Ser His Asp Gly Pro Val Ala Gly Leu Ala Phe Asp Leu
595                 600                 605

AAT GAG CCC TCA GCT GAT GTC TCC TCT GCC TGG GCC CAG          1872
Asn Glu Pro Ser Ala Asp Val Ser Ser Ala Trp Ala Gln
            610                 615                 620

CAT GTC ACC AAG ATG GTG GCT CGG AGA GGA GCC ATA CTG          1911
His Val Thr Lys Met Val Ala Arg Arg Gly Ala Ile Leu
                625                 630

CCC CAG GAT ATT TCT GTC ACC CCT GTG GCA ACT CCA GTG          1950
Pro Gln Asp Ile Ser Val Thr Pro Val Ala Thr Pro Val
635                 640                 645

CCC CCA GAG GAA CAA GCC AAC CTG TGG CTG GTT GAG GCA          1989
Pro Pro Glu Glu Gln Ala Asn Leu Trp Leu Val Glu Ala
        650                 655

GAG ATC TCC CCA GAG CTG CAG AAG CGC CTG GGC CGG AAG          2028
Glu Ile Ser Pro Glu Leu Gln Lys Arg Leu Gly Arg Lys
660                 665                 670

AAG AAG AGG AGG AAG AGG AAG AAG GAG GTG TGC CCG CTG          2067
Lys Lys Arg Arg Lys Arg Lys Lys Glu Val Cys Pro Leu
            675                 680                 685

GCG CCG CCC CCT GAG CTT CAC CCC CCT GCC CCT GCC CCC          2106
Ala Pro Pro Pro Glu Leu His Pro Pro Ala Pro Ala Pro
                690                 695

AGT ACC ATT CCT CGA CTG CCT CAG CTG CCC CGG CAG AAA          2145
Ser Thr Ile Pro Arg Leu Pro Gln Leu Pro Arg Gln Lys
700                 705                 710
```

```
TGC CTG GTG GCT GCA GGT GCC TGG GGA GCT GGG GAC TCT                    2184
Cys Leu Val Ala Ala Gly Ala Trp Gly Ala Gly Asp Ser
            715                 720

TGC CGA CAG GGA GCG TGG ACC CTG GTC TCC AAC CCA TTC                    2223
Cys Arg Gln Gly Ala Trp Thr Leu Val Ser Asn Pro Phe
725                 730                 735

TGC CCA GAG CCC AGT CCC CCT CAG GAT CCA TTT CTG CCC                    2262
Cys Pro Glu Pro Ser Pro Pro Gln Asp Pro Phe Leu Pro
            740                 745                 750

AGT GCA CCG GCC CCC GTG GCA TGG GCT CAT GGC CGC CGA                    2301
Ser Ala Pro Ala Pro Val Ala Trp Ala His Gly Arg Arg
                755                 760

CAG GGC CTG GGG CCT ATT CAC TCC CGC ACC AAC CTG ATG                    2340
Gln Gly Leu Gly Pro Ile His Ser Arg Thr Asn Leu Met
765                 770                 775

GAC ACA GAA CTC ATG GAT GCA GAC TCG GAC TTC TGAGCCT                    2380
Asp Thr Glu Leu Met Asp Ala Asp Ser Asp Phe
            780                 785 787

GCAGAGCAGG ACCTGGGACA GGAAAGAGAG GAACCAATAC CTTCAAGGCT                 2430

CTTCTTCCTC ACCGAGCATG CTTCCCTAGG ATCCCGTCTT CCAGAGAACC                 2480

TGTGGGCTGA CTGCCCTCCG AAGAGAGTTC TGGATGTCTG GCTCAAAGCA                 2530

GCAGGACTGT GGGAAAGAGC CTAACATCTC CATGGGGAGG CCTCACCCCA                 2580

GGGACAGGGC CCTGGAGCTC AGGGTCCTTG TTTCTGCCCT GCCAGCTGCA                 2630

GCCTGGTTGG CAGCATCTGC TCCATCGGGG CAGGGGTAT GCAGAGCTTG                  2680

TGGTGGGGCA GGAACGGTGG AGGCAGAGGT GACAGTTCCC AGAGTGGGCT                 2730

TTGGTGGCCA GGGAGGCAGC CTAGCCTATG TCTGGCAGAT GAGGGCTGGC                 2780

TGCCGTTTTC TGGGCTGATG GGTGCCCTTT CCTGGCAGTC TCAGTCCAAA                 2830

AGTGTTGACT GTGTCATTAG TCCTTTGTCT AAGTAGGGCC AGGGCACCGT                 2880

ATTCCTCTCC CAGGTGTTTG TGGGGCTGGA AGGACCTGCT CCCACAGGGG                 2930

CCATGTCCTC TCTTAATAGG TGGCACTACC CCAAACCCAC CG                         2972

(2) INFORMATION FOR SEQ ID NO:4:

(i) SEQUENCE CHARACTERISTICS:
        (A) LENGTH: 787 amino acids
        (B) TYPE: Amino Acid
        (D) TOPOLOGY: Linear (xi) SEQUENCE DESCRIPTION: SEQ ID NO:4:

Met Ala Ala Ala Arg Pro Ala Arg Gly Pro Glu Leu Pro Leu Leu
1               5                   10                  15

Gly Leu Leu Leu Leu Leu Leu Gly Asp Pro Gly Arg Gly Ala
                20                  25                  30

Ala Ser Ser Gly Asn Ala Thr Gly Pro Gly Pro Arg Ser Ala Gly
                35                  40                  45

Gly Ser Ala Arg Arg Ser Ala Ala Val Thr Gly Pro Pro Pro
                50                  55                  60

Leu Ser His Cys Gly Arg Ala Ala Pro Cys Glu Pro Leu Arg Tyr
                65                  70                  75

Asn Val Cys Leu Gly Ser Val Leu Pro Tyr Gly Ala Thr Ser Thr
                80                  85                  90

Leu Leu Ala Gly Asp Ser Asp Ser Gln Glu Glu Ala His Gly Lys
                95                  100                 105
```

-continued

```
Leu Val Leu Trp Ser Gly Leu Arg Asn Ala Pro Arg Cys Trp Ala
            110                 115                 120

Val Ile Gln Pro Leu Leu Cys Ala Val Tyr Met Pro Lys Cys Glu
            125                 130                 135

Asn Asp Arg Val Glu Leu Pro Ser Arg Thr Leu Cys Gln Ala Thr
            140                 145                 150

Arg Gly Pro Cys Ala Ile Val Glu Arg Glu Arg Gly Trp Pro Asp
            155                 160                 165

Phe Leu Arg Cys Thr Pro Asp Arg Phe Pro Glu Gly Cys Thr Asn
            170                 175                 180

Glu Val Gln Asn Ile Lys Phe Asn Ser Ser Gly Gln Cys Glu Val
            185                 190                 195

Pro Leu Val Arg Thr Asp Asn Pro Lys Ser Trp Tyr Glu Asp Val
            200                 205                 210

Glu Gly Cys Gly Ile Gln Cys Gln Asn Pro Leu Phe Thr Glu Ala
            215                 220                 225

Glu His Gln Asp Met His Ser Tyr Ile Ala Ala Phe Gly Ala Val
            230                 235                 240

Thr Gly Leu Cys Thr Leu Phe Thr Leu Ala Thr Phe Val Ala Asp
            245                 250                 255

Trp Arg Asn Ser Asn Arg Tyr Pro Ala Val Ile Leu Phe Tyr Val
            260                 265                 270

Asn Ala Cys Phe Phe Val Gly Ser Ile Gly Trp Leu Ala Gln Phe
            275                 280                 285

Met Asp Gly Ala Arg Arg Glu Ile Val Cys Arg Ala Asp Gly Thr
            290                 295                 300

Met Arg Leu Gly Glu Pro Thr Ser Asn Glu Thr Leu Ser Cys Val
            305                 310                 315

Ile Ile Phe Val Ile Val Tyr Tyr Ala Leu Met Ala Gly Val Val
            320                 325                 330

Trp Phe Val Val Leu Thr Tyr Ala Trp His Thr Ser Phe Lys Ala
            335                 340                 345

Leu Gly Thr Thr Tyr Gln Pro Leu Ser Gly Lys Thr Ser Tyr Phe
            350                 355                 360

His Leu Leu Thr Trp Ser Leu Pro Phe Val Leu Thr Val Ala Ile
            365                 370                 375

Leu Ala Val Ala Gln Val Asp Gly Asp Ser Val Ser Gly Ile Cys
            380                 385                 390

Phe Val Gly Tyr Lys Asn Tyr Arg Tyr Arg Ala Gly Phe Val Leu
            395                 400                 405

Ala Pro Ile Gly Leu Val Leu Ile Val Gly Gly Tyr Phe Leu Ile
            410                 415                 420

Arg Gly Val Met Thr Leu Phe Ser Ile Lys Ser Asn His Pro Gly
            425                 430                 435

Leu Leu Ser Glu Lys Ala Ala Ser Lys Ile Asn Glu Thr Met Leu
            440                 445                 450

Arg Leu Gly Ile Phe Gly Phe Leu Ala Phe Gly Phe Val Leu Ile
            455                 460                 465

Thr Phe Ser Cys His Phe Tyr Asp Phe Phe Asn Gln Ala Glu Trp
            470                 475                 480

Glu Arg Ser Phe Arg Asp Tyr Val Leu Cys Gln Ala Asn Val Thr
            485                 490                 495
```

-continued

```
Ile Gly Leu Pro Thr Lys Gln Pro Ile Pro Asp Cys Glu Ile Lys
            500                 505                 510

Asn Arg Pro Ser Leu Leu Val Glu Lys Ile Asn Leu Phe Ala Met
            515                 520                 525

Phe Gly Thr Gly Ile Ala Met Ser Thr Trp Val Trp Thr Lys Ala
            530                 535                 540

Thr Leu Leu Ile Trp Arg Arg Thr Trp Cys Arg Leu Thr Gly Gln
            545                 550                 555

Ser Asp Asp Glu Pro Lys Arg Ile Lys Lys Ser Lys Met Ile Ala
            560                 565                 570

Lys Ala Phe Ser Lys Arg His Glu Leu Leu Gln Asn Pro Gly Gln
            575                 580                 585

Glu Leu Ser Phe Ser Met His Thr Val Ser His Asp Gly Pro Val
            590                 595                 600

Ala Gly Leu Ala Phe Asp Leu Asn Glu Pro Ser Ala Asp Val Ser
            605                 610                 615

Ser Ala Trp Ala Gln His Val Thr Lys Met Val Ala Arg Arg Gly
            620                 625                 630

Ala Ile Leu Pro Gln Asp Ile Ser Val Thr Pro Val Ala Thr Pro
            635                 640                 645

Val Pro Pro Glu Glu Gln Ala Asn Leu Trp Leu Val Glu Ala Glu
            650                 655                 660

Ile Ser Pro Glu Leu Gln Lys Arg Leu Gly Arg Lys Lys Lys Arg
            665                 670                 675

Arg Lys Arg Lys Lys Glu Val Cys Pro Leu Ala Pro Pro Pro Glu
            680                 685                 690

Leu His Pro Pro Ala Pro Ala Pro Ser Thr Ile Pro Arg Leu Pro
            695                 700                 705

Gln Leu Pro Arg Gln Lys Cys Leu Val Ala Ala Gly Ala Trp Gly
            710                 715                 720

Ala Gly Asp Ser Cys Arg Gln Gly Ala Trp Thr Leu Val Ser Asn
            725                 730                 735

Pro Phe Cys Pro Glu Pro Ser Pro Pro Gln Asp Pro Phe Leu Pro
            740                 745                 750

Ser Ala Pro Ala Pro Val Ala Trp Ala His Gly Arg Arg Gln Gly
            755                 760                 765

Leu Gly Pro Ile His Ser Arg Thr Asn Leu Met Asp Thr Glu Leu
            770                 775                 780

Met Asp Ala Asp Ser Asp Phe
            785     787
```

(2) INFORMATION FOR SEQ ID NO:5:

(i) SEQUENCE CHARACTERISTICS:
        (A) LENGTH: 1036 amino acids
        (B) TYPE: Amino Acid
        (D) TOPOLOGY: Linear (xi) SEQUENCE DESCRIPTION: SEQ ID NO:5:

```
Met Gln Tyr Leu Asn Phe Pro Arg Met Pro Asn Ile Met Met Phe
 1               5                  10                  15

Leu Glu Val Ala Ile Leu Cys Leu Trp Val Val Ala Asp Ala Ser
                20                  25                  30

Ala Ser Ser Ala Lys Phe Gly Ser Thr Thr Pro Ala Ser Ala Gln
                35                  40                  45
```

-continued

Gln Ser Asp Val Glu Leu Glu Pro Ile Asn Gly Thr Leu Asn Tyr
            50                  55                  60

Arg Leu Tyr Ala Lys Lys Gly Arg Asp Asp Lys Pro Trp Phe Asp
            65                  70                  75

Gly Leu Asp Ser Arg His Ile Gln Cys Val Arg Arg Ala Arg Cys
            80                  85                  90

Tyr Pro Thr Ser Asn Ala Thr Asn Thr Cys Phe Gly Ser Lys Leu
            95                 100                 105

Pro Tyr Glu Leu Ser Ser Leu Asp Leu Thr Asp Phe His Thr Glu
           110                 115                 120

Lys Glu Leu Asn Asp Lys Leu Asn Asp Tyr Tyr Ala Leu Lys His
           125                 130                 135

Val Pro Lys Cys Trp Ala Ala Ile Gln Pro Phe Leu Cys Ala Val
           140                 145                 150

Phe Lys Pro Lys Cys Glu Lys Ile Asn Gly Glu Asp Met Val Tyr
           155                 160                 165

Leu Pro Ser Tyr Glu Met Cys Arg Ile Thr Met Glu Pro Cys Arg
           170                 175                 180

Ile Leu Tyr Asn Thr Thr Phe Phe Pro Lys Phe Leu Arg Cys Asn
           185                 190                 195

Glu Thr Leu Phe Pro Thr Lys Cys Thr Asn Gly Ala Arg Gly Met
           200                 205                 210

Lys Phe Asn Gly Thr Gly Gln Cys Leu Ser Pro Leu Val Pro Thr
           215                 220                 225

Asp Thr Ser Ala Ser Tyr Tyr Pro Gly Ile Glu Gly Cys Gly Val
           230                 235                 240

Arg Cys Lys Asp Pro Leu Tyr Thr Asp Asp Glu His Arg Gln Ile
           245                 250                 255

His Lys Leu Ile Gly Trp Ala Gly Ser Ile Cys Leu Leu Ser Asn
           260                 265                 270

Leu Phe Val Val Ser Thr Phe Phe Ile Asp Trp Lys Asn Ala Asn
           275                 280                 285

Lys Tyr Pro Ala Val Ile Val Phe Tyr Ile Asn Leu Cys Phe Leu
           290                 295                 300

Ile Ala Cys Val Gly Trp Leu Leu Gln Phe Thr Ser Gly Ser Arg
           305                 310                 315

Glu Asp Ile Val Cys Arg Lys Asp Gly Thr Leu Arg His Ser Glu
           320                 325                 330

Pro Thr Ala Gly Glu Asn Leu Ser Cys Ile Val Ile Phe Val Leu
           335                 340                 345

Val Tyr Tyr Phe Leu Thr Ala Gly Met Val Trp Phe Val Phe Leu
           350                 355                 360

Thr Tyr Ala Trp His Trp Arg Ala Met Gly His Val Gln Asp Arg
           365                 370                 375

Ile Asp Lys Lys Gly Ser Tyr Phe His Leu Val Ala Trp Ser Leu
           380                 385                 390

Pro Leu Val Leu Thr Ile Thr Thr Met Ala Phe Ser Glu Val Asp
           395                 400                 405

Gly Asn Ser Ile Val Gly Ile Cys Phe Val Gly Tyr Ile Asn His
           410                 415                 420

Ser Met Arg Ala Gly Leu Leu Leu Gly Pro Leu Cys Gly Val Ile
           425                 430                 435

-continued

```
Leu Ile Gly Gly Tyr Phe Ile Thr Arg Gly Met Val Met Leu Phe
            440                 445                 450

Gly Leu Lys His Phe Ala Asn Asp Ile Lys Ser Thr Ser Ala Ser
            455                 460                 465

Asn Lys Ile His Leu Ile Ile Met Arg Met Gly Val Cys Ala Leu
            470                 475                 480

Leu Thr Leu Val Phe Ile Leu Val Ala Ile Ala Cys His Val Thr
            485                 490                 495

Glu Phe Arg His Ala Asp Glu Trp Ala Gln Ser Phe Arg Gln Phe
            500                 505                 510

Ile Ile Cys Lys Ile Ser Ser Val Phe Glu Glu Lys Ser Ser Cys
            515                 520                 525

Arg Ile Glu Asn Arg Pro Ser Val Gly Val Leu Gln Leu His Leu
            530                 535                 540

Leu Cys Leu Phe Ser Ser Gly Ile Val Met Ser Thr Trp Cys Trp
            545                 550                 555

Thr Pro Ser Ser Ile Glu Thr Trp Lys Arg Tyr Ile Arg Lys Lys
            560                 565                 570

Cys Gly Lys Glu Val Val Glu Val Lys Met Pro Lys His Lys
            575                 580                 585

Val Ile Ala Gln Thr Trp Ala Lys Arg Lys Asp Phe Glu Asp Lys
            590                 595                 600

Gly Arg Leu Ser Ile Thr Leu Tyr Asn Thr His Thr Asp Pro Val
            605                 610                 615

Gly Leu Asn Phe Asp Val Asn Asp Leu Asn Ser Ser Glu Thr Asn
            620                 625                 630

Asp Ile Ser Ser Thr Trp Ala Ala Tyr Leu Pro Gln Cys Val Lys
            635                 640                 645

Arg Arg Met Ala Leu Thr Gly Ala Ala Thr Gly Asn Ser Ser Ser
            650                 655                 660

His Gly Pro Arg Lys Asn Ser Leu Asp Ser Glu Ile Ser Val Ser
            665                 670                 675

Val Arg His Val Ser Val Glu Ser Arg Arg Asn Ser Val Asp Ser
            680                 685                 690

Gln Val Ser Val Lys Ile Ala Glu Met Lys Thr Lys Val Ala Ser
            695                 700                 705

Arg Ser Arg Gly Lys His Gly Gly Ser Ser Ser Asn Arg Arg Thr
            710                 715                 720

Gln Arg Arg Arg Asp Tyr Ile Ala Ala Ala Thr Gly Lys Ser Ser
            725                 730                 735

Arg Arg Arg Glu Ser Ser Thr Ser Val Glu Ser Gln Val Ile Ala
            740                 745                 750

Leu Lys Lys Thr Thr Tyr Pro Asn Ala Ser His Lys Val Gly Val
            755                 760                 765

Phe Ala His His Ser Ser Lys Lys Gln His Asn Tyr Thr Ser Ser
            770                 775                 780

Met Lys Arg Arg Thr Ala Asn Ala Gly Leu Asp Pro Ser Ile Leu
            785                 790                 795

Asn Glu Phe Leu Gln Lys Asn Gly Asp Phe Ile Phe Pro Phe Leu
            800                 805                 810

Gln Asn Gln Asp Met Ser Ser Ser Ser Glu Glu Asp Asn Ser Arg
            815                 820                 825
```

-continued

```
Ala Ser Gln Lys Ile Gln Asp Leu Asn Val Val Val Lys Gln Gln
            830             835                 840
Glu Ile Ser Glu Asp Asp His Asp Gly Ile Lys Ile Glu Glu Leu
            845             850                 855
Pro Asn Ser Lys Gln Val Ala Leu Glu Asn Phe Leu Lys Asn Ile
            860             865                 870
Lys Lys Ser Asn Glu Ser Asn Ser Asn Arg His Ser Arg Asn Ser
            875             880                 885
Ala Arg Ser Gln Ser Lys Lys Ser Gln Lys Arg His Leu Lys Asn
            890             895                 900
Pro Ala Ala Asp Leu Asp Phe Arg Lys Asp Cys Val Lys Tyr Arg
            905             910                 915
Ser Asn Asp Ser Leu Ser Cys Ser Ser Glu Glu Leu Asp Val Ala
            920             925                 930
Leu Asp Val Gly Ser Leu Leu Asn Ser Ser Phe Ser Gly Ile Ser
            935             940                 945
Met Gly Lys Pro His Ser Arg Asn Ser Lys Thr Ser Cys Asp Val
            950             955                 960
Gly Ile Gln Ala Asn Pro Phe Glu Leu Val Pro Ser Tyr Gly Glu
            965             970                 975
Asp Glu Leu Gln Gln Ala Met Arg Leu Leu Asn Ala Ala Ser Arg
            980             985                 990
Gln Arg Thr Glu Ala Ala Asn Glu Asp Phe Gly Gly Thr Glu Leu
            995             1000                1005
Gln Gly Leu Leu Gly His Ser His Arg His Gln Arg Glu Pro Thr
            1010            1015                1020
Phe Met Ser Glu Ser Asp Lys Leu Lys Met Leu Leu Leu Pro Ser
            1025            1030                1035
Lys
1036
```